(12) United States Patent
Senna et al.

(10) Patent No.: US 8,940,304 B2
(45) Date of Patent: Jan. 27, 2015

(54) **MONOCLONAL ANTIBODIES AGAINST THE PBP2-A PROTEIN AND HOMOLOGOUS SEQUENCES FOR THE TREATMENT OF INFECTIONS BY AND IMMUNODIAGNOSTICS OF BACTERIA OF THE *FIRMICUTES* PHYLUM**

(75) Inventors: Jose Procopio Moreno Senna, Rio de Janeiro (BR); Joao Luiz Sampaio Queiroz, Rio de Janeiro (BR); Nadia Maria Batoreu, Rio de Janeiro (BR); Maria da Gloria Martins Teixeira, Rio de Janeiro (BR)

(73) Assignee: Fundaco Oswaldo Cruz, Rio de Janiero (BR)

( * ) Notice: Subject to any disclaimer, the term of this patent is extended or adjusted under 35 U.S.C. 154(b) by 0 days.

(21) Appl. No.: 13/389,860

(22) PCT Filed: Aug. 10, 2010

(86) PCT No.: PCT/BR2010/000263
§ 371 (c)(1),
(2), (4) Date: Apr. 18, 2012

(87) PCT Pub. No.: WO2011/017791
PCT Pub. Date: Feb. 17, 2011

(65) Prior Publication Data
US 2012/0195907 A1      Aug. 2, 2012

(30) Foreign Application Priority Data
Aug. 10, 2009   (BR) ..................................... 0914508

(51) Int. Cl.
*C07K 16/00*   (2006.01)
*C07K 16/12*   (2006.01)

(52) U.S. Cl.
CPC ......... *C07K 16/1271* (2013.01); *C07K 2317/56* (2013.01); *C07K 2317/565* (2013.01)
USPC .................................... 424/150.1; 530/388.2

(58) Field of Classification Search
None
See application file for complete search history.

(56) References Cited

FOREIGN PATENT DOCUMENTS

| WO | WO 2007/110475 | * 11/2005 |
| WO | 2006/081171 | * 8/2006 |
| WO | 2006081171 | * 8/2006 |

OTHER PUBLICATIONS

Saito et al (Journal of Clinical Microbiology 33(9):2498-2500, 1995).*
Bendig (Methods: A Companion to Methods in Enzymology 1995; 8:83-93).*
Stedman's Online Medical Dictionary (http://www.stedmans.com/section.cfm/45) defines invasion as—invasion.*
Dorland's Medical Dictionary for Healthcare Consumers (http://www.mercksource.com/pp/us/cns/cns_hl_dorlands_split.jsp?pg=/ppdocs/us/common/dorlands/dorland/four/000053439.htm) defines—infection.*
The Online Medical Dictionary (http://cancerweb.ncl.ac.uk/cgi-bin/omd?infection) defines infection.*

* cited by examiner

*Primary Examiner* — Patricia A Duffy
(74) *Attorney, Agent, or Firm* — Caesar, Rivise, Bernstein, Cohen & Pokotilow, Ltd.

(57) ABSTRACT

The present invention relates to monoclonal antibodies capable of recognizing and binding to the PBP2-a protein and to other proteins having sequences homologous to PBP2-a, including pathogenic species such as the methyciline-resistant *Staphylococcus Aureus* (MRSA), coagulase-negative *Staphilococcus, Staphylococcus sciuri* and *Enterococcus*, and any other bacteria containing the PBP2-a protein or homologous sequences. The invention also relates to the use of the monoclonal antibodies capable of recognizing and binding to the PBP2-a protein and to other proteins having sequences homologous to PBP2-a in a complementary immunodiagnostic test for detecting resistance to beta-lactam antibiotics.

5 Claims, 9 Drawing Sheets

Quantification renal CEB MRSA

Log bact

Quantification renal Iberian MRSA

Quantification renal CA-MRSA WB79

MONOCLONAL ANTIBODIES AGAINST THE PBP2-A PROTEIN AND HOMOLOGOUS SEQUENCES FOR THE TREATMENT OF INFECTIONS BY AND IMMUNODIAGNOSTICS OF BACTERIA OF THE *FIRMICUTES* PHYLUM

INVENTION FIELD

The current invention refers to monoclonal antibodies able to recognize and bind to PBP2a protein and other proteins presenting sequences homologous to PBP2a, including the pathogens methicillin-resistant *Staphylococcus aureus*-MRSA, coagulase-negative *Staphylococcus*, *Staphylococcus sciuri*, *Enterococcus* spp., and any other bacterium possessing PBP2a or sequences homologous to this protein.

The invention still refers to the use of monoclonal antibodies able to recognize and bind to PBP2a protein and other proteins presenting sequences homologous to PBP2a in a complementary immunodiagnosis for detection of resistance to beta-lactams.

INVENTION RATIONALES

Infections caused by methicillin-resistant *Staphylococcus aureus* (MRSA) are a major concern cause for clinicians, presenting mortality and morbidity rates higher than the ones of infections caused by methicillin-sensitive Staphylococci (1). Furthermore, these infections cause longer hospitalization time and higher expense with antimicrobials, leading to a higher cost in treatment of patients infected by this pathogen (1). Vancomycin has been the first choice antimicrobial for treatment of infections caused by MRSA. However, the growing isolation of MRSA strains in communities in the United States and Australia (2, 3, 4), together with the identification of MRSA strains with intermediate resistance to vancomycin in Japan, United States (5), and Brazil (6), cause the current scene to become more severe. The description of MRSA strains totally resistant to vancomycin in 2004 (7) has caused huge concern in the medical-scientific community. MRSA now represents a strong candidate for becoming the fearful "superbug or superbacterium"—a pathogen resistant to all drugs available nowadays.

Usually, MRSA prevalence rates (ratio of all infections by *S. aureus* caused by MRSA) in hospital infections are gradually increasing in the last decades. In a study conducted by Jarvis et al., including 1268 ICUs (intensive care units) in 337 hospitals in the United States, the number of infections by MRSA in ICUs changed from 660 to 2184 cases and the prevalence increased from 35% to 64.4% (8): In Japan, prevalence rates of hospital infections (HIs) caused by MRSA can present worrying values, from 60% to 90% (9). In studies conducted in the United States, the percentile changed from 2% in 1974 to 50% in 1997 (10, 11) and, in some hospitals in the United States, more than 80% of HIs are caused by MRSA (12). In England, the prevalence increased from 1.5% to 15.2% between 1989 and 1995 and now (2004) the estimate is 41.5% (13).

Besides high prevalence rates, especially in teaching and large-sized hospitals, MRSA is deemed as the main pathogen causing epidemic outbreaks in Brazilian hospitals (14). In 1986, more than 50% of *S. aureus* strains with hospital origin isolated in patients from university hospitals in São Paulo were resistant to methicillin and, in 1993, the incidence of MRSA in the Pediatric Hospital of Paulista Medicine School was 70% (15). In a study conducted in hospitals in Belo Horizonte, Resende et al. (16) pointed out a prevalence of 71% of MRSA.

MRSA strains present a penicillin-binding protein with very low affinity for antimicrobials in the beta-lactam class, such as PBP2a (17). In the presence of this enzyme, which is codified by gene mecA, the bacterium is successful to synthesize the peptidoglycan, even in the presence of beta-lactams. This enzyme can be also found in coagulase-negative *Staphylococcus* and in *Staphylococcus sciuri*—a bacterium present in the normal flora of dogs. Besides resistance to beta-lactams, hospital MRSA strains present resistance to most other available antimicrobial classes, with the use of glycopeptides (vancomycin and teicoplanin) remaining as first choice treatment.

Two studies using DNA vaccine against PBP2a showed that this protein is immunogenic and that the obtained immune response was able to confer protection against MRSA in assays conducted in murine model (18, 19). However, it is known that, in hospital infections, most patients are immunodepressed (20). In this cases, a vaccine would not be able to generate protective antibodies in due time to control a bacterial infection.

PBP2a Immunogenicity

PBP2a is a class II multimodular enzyme according to Goffin and Ghuysen's classification (40). This 76-kilodalton enzyme is composed by a membrane-binding region, a non-transpeptidase domain, and a transpeptidase domain, containing a 4-amino acid active core (STQK), responsible for the bacterial transpeptidation reactions (20 bis Ryfell, 1990).

State of the art studies with the DNA vaccine against PBP2a show that the results of bacterial reduction (renal quantification) in immunized animals subjected to challenge by systemic infection were of 3 to 4 times in the work of Ohwada et al. and of 1000 times in the work of Senna et al. The authors of these studies used the full sequence (except the membrane fixation region) of the gene mecA and an internal fragment of transpeptidase domain, respectively.

But, according to what was mentioned above, a vaccine is not able to generate protective antibodies in due time to control a bacterial infection. Thus, in case of infections by MRSA, the administration of anti-PBP2a monoclonal antibodies is the most proper therapy for treating these infections.

INVENTION SUMMARY

The main objective of the current invention is to provide monoclonal antibodies able to recognize and to bind to PBP2a protein (SEQ ID NO.:1) and other proteins presenting sequences homologous to PBP2a, including the pathogens methicillin-resistant *Staphylococcus aureus*-MRSA, coagulase-negative *Staphylococcus*, *Staphylococcus sciuri*, *Enterococcus* spp., and any other bacterium possessing PBP2a or sequences homologous to this protein.

Another invention objective is the use of monoclonal antibodies able to recognize and bind to the PBP2a protein and other proteins presenting sequences homologous to PBP2a in a complementary immunodiagnosis for detection of resistance to beta-lactams.

The monoclonal antibodies of the current invention are represented by sequences SEQ ID NO.: 6, SEQ ID NO.: 7, SEQ ID NO.: 8, SEQ ID NO.: 9, SEQ ID NO.: 10, SEQ ID NO.: 11, SEQ ID NO.: 12, SEQ ID NO.: 13, SEQ ID NO.: 14, SEQ ID NO.: 15, SEQ ID NO.: 16, and SEQ ID NO.: 17.

BRIEF FIGURE DESCRIPTION

Figure 12:
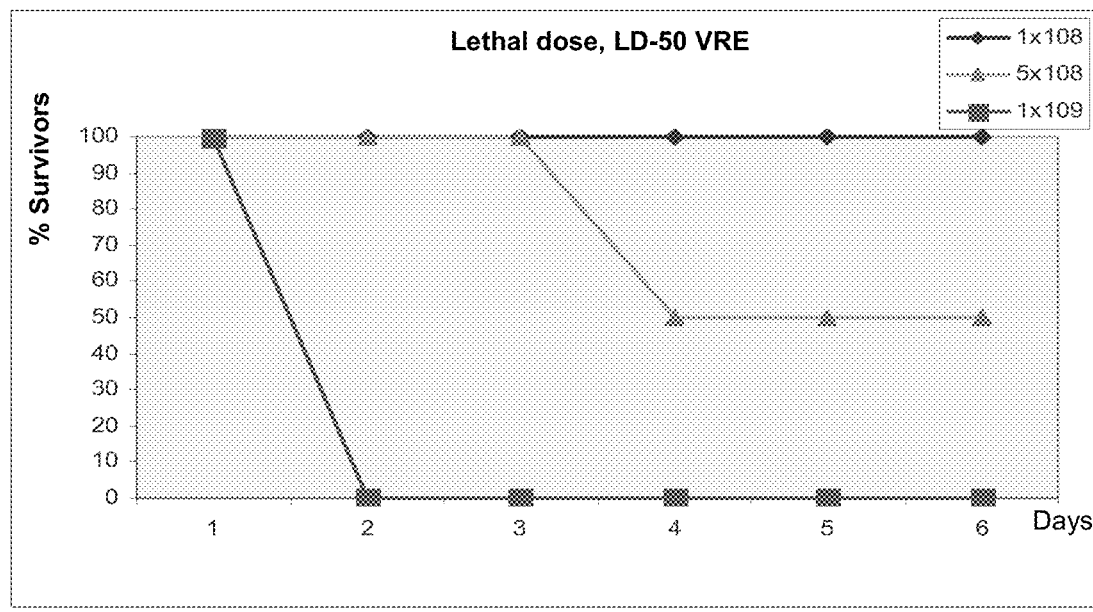

FIG. 12 refers to $LD_{50}$ and lethal dose for intraperitoneal infection determination.

Figure 13:
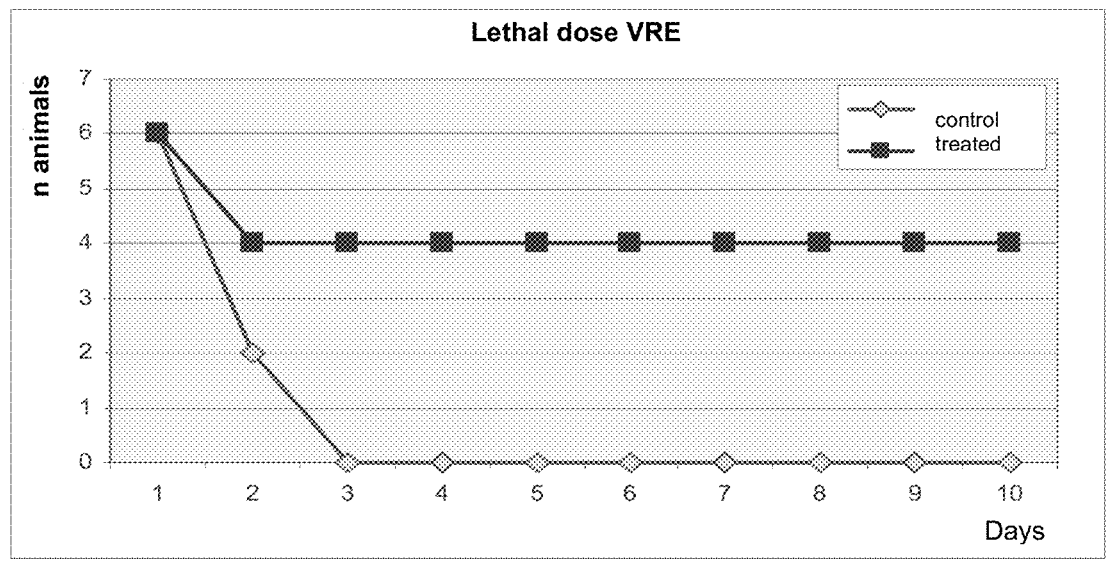

FIG. 13 shows the efficacy result of in vivo protection of anti-PBP2a and PBP5 monoclonal antibody from enterococci against systemic infection.

Figure 14:
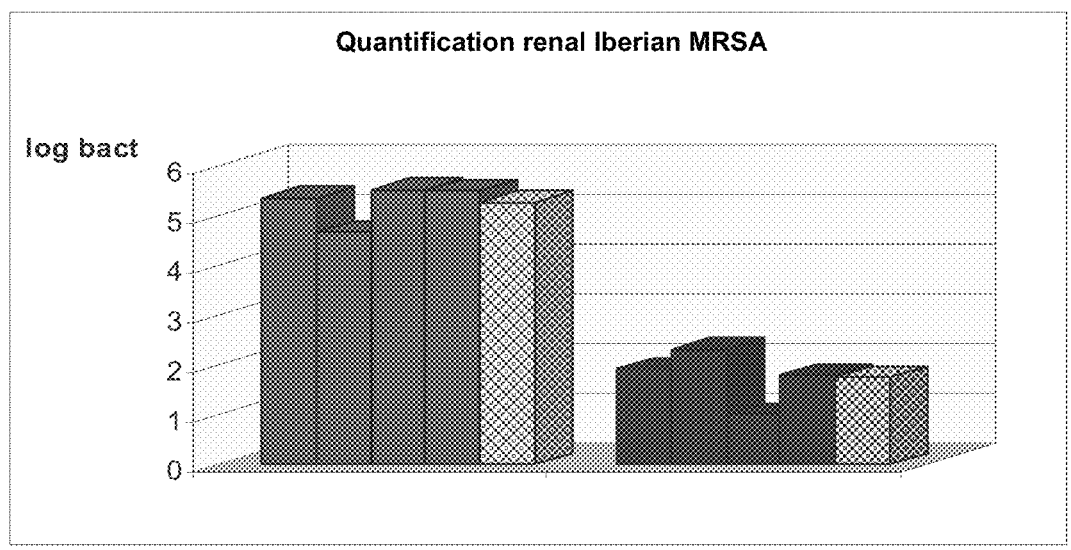

FIG. 14 shows results of the in vivo protection test—systemic infection by intraperitoneal route in murine model with vancomycin-resistant *Enterococcus faecium*.

DETAILED INVENTION DESCRIPTION

The emergence of infections by bacteria multiresistant to antimicrobials is presenting an alarming increase. The prevalence of hospital infections caused by MRSA has increased in all world parts present high morbidity and cause high cost due to the intensive use of antimicrobials and to the longer period of patient hospitalization (24). The treatment based on chemotherapy has been showing signs of exhaustion, with appearance of very few really novel and efficient drugs in the market (25).

In this context, passive immunotherapy (re)appears as a promising alternative, presenting a range of advantageous features compared to conventional chemotherapy: among them, the lower toxicity, higher plasma half-life (which facilitates the treatment by dose reduction and maybe a lower final treatment cost), and, especially in the case of the product presented here, selective toxicity, recommended by Paul Ehrlich (where the drug selectively eliminates the referred pathogen) (25a). This last feature is extremely useful to prevent the so called selection pressure, played by broad-spectrum antimicrobials—which provides the appearance of multiresistant bacteria (26).

In order to develop this product, the inventors selected PBP2a as target, based on preliminary studies with DNA vaccine in murine models (18, 19, 21) and immunostructural molecule analyses. PBP2a had its structure elucidated in 2002 (29), and is deposited at PDB (Protein Data Bank) under the code 1wmr.

Differently from other approaches, the inventors worked with an internal region of the molecule with 76 amino acids, which flank the enzyme active core (SxxK), at the transpeptidase domain. Epitope identification analyses were performed at the molecule and in their presentation to the different class II CHM alleles (Tepitope program), with later verification of their location at the molecule (SPDB-Viewer program). This approach enables us to evaluate the facility of antibody access to these targets at the native molecule.

This computerized analysis showed the presence of epitopes close to the enzyme active core, with excellent recognition degree by class II CHM alleles, located at PBP2a surface (not shown data).

These in silico previews were confirmed by the performed target recognition tests (immunoblotting and flow cytometry), and the antibody binding to this PBP2a region showed to be able to confer high protection, demonstrated by the results obtained in the performed in vitro and in vivo tests. The antibodies generated by the 76-amino acid fragment showed to confer higher protection than the ones generated by immunization with full PBP2a, as previously shown by Ohwada and Senna's works and were confirmed by the results from the inventors.

The epidemiology of infections caused by MRSA shows the presence of the predominant clonal types, responsible for outbreaks and epidemics in hospitals in the whole world. These clones present a higher colonization and virulence capacity when compared to non-epidemic MRSA strains (30).

As a way to validate the obtained results, it was intended to work with different MRSA clones (epidemic clones), representatives from most infections (especially the hospital ones) caused by MRSA.

CEB strain (Brazilian epidemic clone) is responsible for most infections caused by MRSA in Brazilian hospitals (31), being also identified in other countries in South America (32, 33), Portugal, and Czechoslovakia (34). The European epidemic clone (Iberian-MRSA) is found in European countries and in the United States (35).

Due to the increase in cases of community infections caused by MRSA, one of these strains (WB79 CA-MRSA), isolated in Brazil, was included in the current trials. These trials present features differentiated from the ones found in hospitals, with higher virulence (presence of Panton-Valentine leukocidin) and profile of resistance to antimicrobials different from the one of hospital MRSA strains (36).

Recently, an outbreak of infections by CA-MRSA in a population of men practicing sex with other men was identified in the United States (37). From this date, we can say that infections caused by MRSA assume a STD (sexually transmitted disease) character.

The protection results conferred by administration of anti-PBP2a antibody showed efficacy against all the different tested clones, which led us to believe in their applicability for infections (community or hospital) caused by any MRSA type.

Some significant features of the product of the current invention need to be commented.

(i) In vitro protection results cause to believe that the involved mechanism of action—block of a region close to the molecule active core—is sufficient to inhibit the bacterial growth and multiplication. Similarly to the one of beta-lactam antibiotics, this mechanism is time-dependent, needing that the bacterium is in the multiplication phase to expose the target to the drug action.

(ii) This feature is favored by the pharmacokinetic properties of antibodies, which present long plasma half-life (38). Comparing to the antibiotic therapy, this means an administration in lower number of doses, presenting treatment facility for the patient and maybe lower final cost as consequences. These ideas were confirmed in practice in the protection comparative assay with vancomycin (see below).

(iii) The inhibition of in vitro bacterial growth also means that the antibody does not need the traditional ancillary antigen-antibody response mechanisms, such as opsonization and complement activation. Considering that most hospital infections occur in patients that has immunodepression status, this product feature is extremely significant.

(iv) It is known that *Staphylococcus aureus* presents a protein A on its surface. This molecule characteristically binds itself to the Fc region of immunoglobulins, impeding the opsonizing activity of the immune system (38). Due to the results obtained in our trials, we believe that the administered antibody concentration was able to saturate the protein A existing at the bacterial surface, not preventing the PBP2a block by the administered antibodies.

Systemic infections caused by MRSA have been treated with use of glycopeptides, especially vancomycin. However, this drug presents a range of side effects, with immunotoxicity (42), ototoxicity, nephrotoxicity, and transient neutropenia (43) among them, and need administration for long periods, presenting high final treatment cost.

By using a murine infection model, it was possible to compare a treatment with vancomycin versus monoclonal antibody and the combination of the two drugs. The obtained results indicated that an antibody dose had action similar to or higher than 5 vancomycin doses and that the simultaneous administration of the two drugs was very more efficient in eliminating the bacterium than the isolated administration. These data are extremely significant, as it is possible to think about a lower treatment cost with the antibody and a more efficient recovery of patients with severe status with the administration of vancomycin and antibody.

In addition to the use of anti-PBP2a monoclonal antibodies for treating infections by MRSA, the current invention still considers the following applications:

(i) the results of recognition of a protein with molecular weight close to the one of PBP5 in *Enterococcus* sp. strain by anti-PBP2a monoclonal antibody indicate that it is possible to obtain a protective response against this pathogen with the antibody administration. PBP5 presents homology with PBP2a, with both being classified as class B multimodular PBPs, with low affinity for beta-lactams (40). Enterococci are bacteria that cause severe hospital infections, presenting high degree of intrinsic and acquired resistance to antimicrobials. Strains resistant to vancomycin (VRE) represent a reservoir of genes of resistance to glycopeptides and can be transferred to other pathogens (41).

(ii) these antibodies can have applicability for PBP2a identification by immunodiagnostic tests. For example, the use of immune tests based on agglutination of latex particles bound to the antibody can provide a result that foresees resistance to all beta-lactam antibiotics in few hours. In the conventional tests of sensitivity to antimicrobials (such as antibiotic sensitivity testing), these results are only released after 12 to 24 hours.

(iii) once monoclonal antibodies have been successfully used in topic applications against chronic sores (infliximab, see reference Streit et al., and WO 1999041285 A1), these antibodies might be topically administered to promote nasal decolonization by MRSA and for treatment of skin lesions caused by this pathogen.

Based on the knowledge and issues found in the state of art, the current inventor performed immunizations in animals with a DNA vaccine with constructions corresponding to the gene mecA (SEQ ID NO.: 2) without the membrane fixation region and immunizations with a 76-amino acid internal region of the transpeptidase domain (SEQ ID NO.: 3) comprising the enzyme active core.

The immunizations were performed in the same conditions presented in the works of Ohwada et al. and Senna et al., who developed a DNA vaccine against PBP2a, using the full sequence (except the membrane fixation region) of the gene mecA and an internal fragment of the transpeptidase domain. The immunizations were performed with 4 doses, and the immunized animals and a non-immunized control group were challenged by a systemic infection with MRSA and a determination of the number of bacteria present in the kidneys of animals in two distinctive periods. The obtained results showed that the immunization with the transpeptidase fragment conferred a greater reduction in the number of bacteria present in the animal kidneys than the one in the animals immunized with gene mecA.

Thus, we see that the antibodies generated against the transpeptidase fragment provided a better protection in the used conditions (DNA vaccine in murine model) than the one by antibodies against PBP2a. The transpeptidase fragment includes the enzyme active core STQK (SEQ ID NO.: 4).

Consequently, based on the found results, the inventors directed the invention for producing monoclonal antibodies able to recognize and bind to the PBP2a protein and other proteins presenting sequences homologous to PBP2a protein and using the transpeptidase fragment that includes the enzyme active core.

The invention will be now described with reference to examples, which must not be considered as limiting.

Example 1

Materials and Methods

1. Bacteria:

The following methicillin-resistant *Staphylococcus aureus* strains were used: Iberian-MRSA, COL-MRSA (ceded by Unité des Agents Antimicrobiens—Institut Pasteur [Unit of Antimicrobial Agents—Pasteur Institute], Dr. Patrice Courvalin), WB79 CA-MRSA, and CEB-MRSA (ceded by Dr. Agnes Figueiredo, Instituto de Microbiologia [Microbiology Institute] of UFRJ); a vancomycin-resistant *Enterococcus*

*faecalis* strain; and a methicillin-sensitive *Staphylococcus aureus* (MSSA) strain. *Escherichia coli* strains BL21 DE3 (Novagen) and TOP10 (Invitrogen) were also used as control.

2. Animals:

Female Balb/C mice, 4 to 8 weeks old, obtained from CECAL-FIOCRUZ and housed at LAEAN-BioManguinhos were used in the immunization and in vivo protection assays.

3. Immunization:

The mice (4 animals) received an initial dose of 100 micrograms of pCI-Neo plasmid: fragment of MRSA mecA gene (18), followed by a 10-microgram dose of purified recombining protein 14 days later, corresponding to an internal region of the MRSA PBP2a (21), emulsified in complete Freund adjuvant, followed by other dose 14 days later, emulsified in incomplete Freund adjuvant. Fourteen days later, the animal with best immune response (evaluated by enzyme immunoassay—ELISA) received an intravenous dose of 10 micrograms of purified protein diluted in PBS (phosphate buffered saline). Three days after the IV injection, the animal was subjected to euthanasia by asphyxia in $CO_2$ (CEUA L0009-07 Protocol—FIOCRUZ), and the spleen was aseptically removed for cell fusion. The serum of the animal with best immune response was used as positive control for other immunological tests.

4. Production of Monoclonal Antibodies:

Lymphocytes removed from spleen were subjected to fusion with SP2/0-Ag14 myeloma cells (ATCC 1581), using polyethylene glycol for fusion, and were cultured in hypoxanthine-aminopterin-thymidine medium at 37° C. in atmosphere of 10% $CO_2$, according to the protocol for producing monoclonal antibodies in *Current Protocols in Immunology* (22). The resulting hybridomas were evaluated by ELISA test after 14 days, using the purified recombining protein as antigen, according to what is described below. The best hybridomas were subjected to cloning, with selection of the best clones by ELISA and these latter being stored in liquid nitrogen.

5. Enzyme Immunoassay—ELISA:

Maxisorb 98-well plastic plates were sensitized with 500 nanograms/well of recombining protein (PBP2a fragment) in carbonate/bicarbonate buffer and incubated at 4° C. for the whole night. In the following day, the plates were washed three times with PBS containing 0.05% of Tween 20 and blocked in PBS and 5% skimmed milk for two hours at 37° C. The samples to be analyzed (serum of immunized animals diluted at 1:100 or cell culture supernatants), and incubated for 2 hours at 37° C. were used. The plate was washed three times with PBS and Tween 20 (0.05%) again, and the anti-Ig conjugate (anti-mouse HRP Ig SIGMA A 0412) was added at 1:5000 dilution, followed by incubation at 37° C. for 90 minutes. After this period, the plate was washed three times with PBS and Tween 20 (0.05%), with addition of TMB peroxidase color developer (BioRad) and incubation for 15 minutes protected from light. The reaction was interrupted by addition of 0.5 N $H_2SO_4$, and the reading was performed at 450 nm. A 1:200 diluted hyperimmune polyclonal serum was used as positive control.

5.1. Avidity Assays Based on Enzyme Immunoassay 5.1.1. Avidity Assay with Urea (Niederhouser et al.—5.1):

The protocol is similar to the immunoassay one (5), with the following modifications: after the sample incubation (100 ng of clone 10 purified monoclonal antibody and 2.0 ng of clone 38 purified monoclonal antibody) for two hours at 37° C., the samples were subjected to three washings with 8 M urea in PBS and Tween 20 (0.05%), followed by four washings in PBS and Tween 20 (0.05%), presenting the same normally processed sample (without treatment with urea) as control. After the reading of sample optical densities, the avidity rate was calculated by the ratio of the reading with urea divided by the reading without urea, multiplied by 100 (percentile result).

5.1.2. Avidity Assay with Ammonium Thiocyanate (Goldblat et al.—5.2)

The protocol is similar to the immunoassay one (5), with the following modifications: after the sample incubation (100 ng of clone 10 purified monoclonal antibody and 2.0 ng of clone 38 purified monoclonal antibody) for two hours at 37° C., the samples were subjected to treatment with ammonium thiocyanate for 30 minutes at 37° C. in the following concentrations: 3 M; 1.5 M; 1.0 M; 0.75 M; 0.50 M; 0.25 M; and 0.125 M. A sample non-treated with ammonium thiocyanate was used as control for each clone.

After the reading of sample optical densities, the avidity rate was calculated by the following formula: AR (avidity rate)=$[(\log 50-\log A)\times(B-A)/\log B-\log A]+A$; where log 50=1.70. A is the lowest ammonium thiocyanate concentration that results in an absorbance reduction lower than 50%, and B is the highest ammonium thiocyanate concentration that results in an absorbance reduction higher than 50%.

6. Monoclonal Antibody Production and Purification:

A sample of previously selected clones 10 and 38 was grown in a serumless medium (GIBCO VP-SFM) with addition of 1% BSA in 100-mL vials in a stove with atmosphere of 10% $CO_2$. The supernatants were subjected to centrifugation, followed by filtration in 0.22-micrometer filters and purified in high performance chromatography (HPLC) with SelectSure protein A MAB resin (GE). The antibodies were neutralized at pH 7.0 with 1 M Tris, pH 10.0, dialyzed against PBS 0.5× in deionized water. The samples were subjected to lyophilization process, resuspended in deionized water, quantified by the Lowry method, and evaluated by electrophoresis in polyacrylamide gel.

7. Target Recognition:

7.1. In vitro PBP2a Recognition—Immunoblotting:

A MRSA (CEB) strain, a methicillin-sensitive *Staphylococcus aureus* (MSSA) strain, a vancomycin-resistant *Enterococcus faecium* strain, and the BL-21 DE3 *Escherichia coli* strain were grown in exponential phase. One mL of each sample was centrifuged and lysed by agitation in glass beads in a mini-Bead Beater device (Biospect Products), 3 times for 30 seconds. One aliquot of each sample was subjected to electrophoresis in 12% denaturing polyacrylamide gel (SDS-PAGE), and the proteins were later transferred to a nylon membrane (Hybond N-BioRad). The membrane was blocked under mild agitation for two hours in PBS buffer containing 10% skimmed milk and 1% BSA (bovine serum albumin). The membrane was washed three times in PBS and Tween 20 (0.05%) and three times in PBS. Then, the latter was placed in incubation for two hours, with supernatant of anti-PBP2a monoclonal antibody diluted in PBS at 1:1 ratio. After the incubation, the membrane was washed as previously described, and the alkaline phosphatase conjugate (murine anti-IgG antibody—Sigma A3688) at 1:15,000 ratio and incubated for ninety minutes. After this period, the washing in PBS was performed again, and the development with Western Blue substrate for alkaline phosphatase (Promega) was performed.

7.2. PBP2a Recognition at the Bacterium Surface—Flow Cytometry:

A MRSA (CEB) strain was grown in stationary (ON) or exponential phase. The samples were washed in PBS 1× and resuspended at a $DO_{600}$ of 0.6 (~$10^8$ bacteria/mL). These latter were centrifuged in 1 mL ($10^8$ bacteria) and resuspended in 0.5% BSA and a 1:10 dilution of normal serum (murine/human). Then, the samples were incubated for 30 min at 4° C., and later, the concentrates (pellets) were washed 2 times in PBS and resuspended in 100 microliters of PBS containing 0.5% BSA and a 1:10,000 dilution of anti-PBP2a monoclonal antibody and incubated for 30 minutes at 4° C. After this step, the samples were washed as previously again and resuspended in 100 microliters of PBS and 0.5% BSA and a dilution (1:1000) of PE (phycoerythrin) mouse anti-Ig conjugate, later being incubated at dark for 30 min at 4° C. Then, the samples were washed again and fixated for 15 minutes at 4° C. in PBS containing 2% paraformaldehyde. After this preparation, the samples were analyzed in a flow cytometer (Becton and Dickinson—FACScalibur).

8. In Vitro Protection Assays—Determination of Minimum Inhibitory Concentration:

MSRA strains (CEB, Iberian, COL, and CA) were grown in exponential phase up to 600 nm of optical density equal to 0.5. The applied inoculum was adjusted for containing approximately 100,000 bacteria. Müller Hinton broth, bacterial inoculum, and growing amounts of purified anti-PBP2a monoclonal antibody were added to test tubes or 24-cavity plates. The plates or tubes were subjected to incubation at 37° C. for 12 hours. After this period, presence or absence of turbidity was observed in the samples. The minimum inhibitory concentration was considered as the lower antibody amount able to inhibit the bacterial inoculum growth (100, 000 bacteria).

9. In Vivo Protection Assays:

9.1. Determination of Lethal Dose and $LD_{50}$ for MRSA Strains.

The determination of lethal dose and $LD_{50}$ were performed according to the Reed-Muench method (23) for MRSA strains (CEB, Iberian, WB79 CA, and COL). Groups of 8-week female Balb/C mice were inoculated by intraperitoneal route with growing bacteria doses and observed for 7 days. The animals that survived after this period were subjected to euthanasia, according to the established animal welfare rules.

9.2. Systemic Infection and Bacterial Renal Quantification Assays.

MRSA strains (CEB, Iberian, and WB79 CA) were grown in exponential phase ($DO_{600}$~0.6), washed and resuspended in sterile PBS 1× at $DO_{600}$~0.5, corresponding to approximately $2\times10^8$ bacteria. This concentration was calculated by dilution and seeding on BHI agar plates containing 10 micrograms of oxacillin/mL. Female 8-week Balb/C mice received one intraperitoneal dose of 400 micrograms of purified anti-PBP2a monoclonal antibody in the first day. In the sixth day, the animals were subjected to euthanasia and the kidneys were aseptically removed. Then, the kidneys were homogenized in 1 mL of sterile Luria broth and successively diluted in series of 10. One hundred microliters of each dilution were seeded on BHI agar plates containing 10 micrograms/mL of oxacillin and incubated for 24 hours at 37° C., with a count of resulting colonies and calculations of total dilutions being performed.

9.3. Survival Assay.

MRSA strains were grown in the same previously described conditions, but an inoculum adjustment was performed for the previously established $LD_{50}$. Female 8-week Balb/C mice received one intraperitoneal dose of 500 micrograms of purified anti-PBP2a monoclonal antibody in the first day. In the following day, these animals plus a control group were infected with one dose of about 2.5 to $6.0\times10^8$ bacteria by intraperitoneal route, according to the $LD_{50}$ of each strain. The animals were observed for 10 days, with the survivors being subjected to euthanasia.

10. Comparative in Vivo Protection Study of Anti-PBP2a Monoclonal Antibody and Vancomycin—Renal Quantification Assay I Four groups of female 8-week Balb/C mice (4 animals per group) received an infective dose of $6.0\times10^7$ bacteria (CEB-MRSA) by intraperitoneal route. The animals received doses of purified monoclonal antibody (MAB), vancomycin, MAB+vancomycin, and negative control, according to the groups below:

group 1: MAB (400 micrograms) (first day)
group 2: vancomycin (150 micrograms, intramuscular route, 12/12 hours)
group 3: vancomycin+MAB (350 micrograms) (1 day after infection)
group 4: control The first doses of antibody and vancomycin were administered 4 hours after the administration of the infective dose. The animals were subjected to euthanasia in the fourth day, and the kidneys were aseptically removed and subjected to renal qualification, according to what was previously described.

Assay II

This assay was performed in the same way as the previous one, but, with a lower infective dose ($7.0\times10^6$ bacteria), with the group 1 being treated with 500 micrograms of purified monoclonal antibody; group 2 being treated with vancomycin (150 micrograms, intramuscular route, 12/12 hours; 5 doses); group 3 being treated with vancomycin+500 micrograms of monoclonal antibody; and group 4 being control (non-treated animals).

11. Identification Complementarity—Determining Regions (CDRs) of Light and Heavy Chains of the Anti-PBP2a Monoclonal Antibody 11.1. mRNA Extraction from Hybridoma Cells A 10-mL centrifugate (pellet) of a cell culture of monoclonal antibody-producing hybridoma was processed for mRNA extraction using the RNeasy Minikit kit (Qiagen).

11.2. cDNA Obtainment

Reverse transcriptase reaction: M-MLV reverse transcriptase kit (Invitrogen) was used for obtaining complementary DNA, following the manufacturing guidelines.

11.3. Amplification of VH and VL Chains by Polymerase Chain Reaction (PCR)

The reactions were performed using the starter sequences (primers) below.

| SEQ ID NO. | Sequence | Use |
|---|---|---|
| | FOR HEAVY CHAIN | |
| 18 | 5' ATG(GA) A(GC)TT(GC) (TG)GG(TC)T(AC)A(AG)CT(GT)G(GA)TT 3' | VH Amplification |
| 19 | 5' ATG(GA)AATG(GC)A(GC)CTGGT(CT)(TA)T(TC)CTCT 3' | VH Amplification |
| 10 | 5' GATGTGAAGCTTCAGGAGTC 3' | VH Amplification |
| 21 | 5' CAGGTGCAGCTGAAGGAGTC 3' | VH Amplification |
| 22 | 5' CAGGTGCAGCTGAAGCAGTC 3' | VH Amplification |
| 23 | 5' CAGGTTACTCTGAAAGAGTC 3' | VH Amplification |
| 24 | 5' GAGGTCCAGCTGCAACAATCT 3' | VH Amplification |
| 25 | 5' GAGGTCCAGCTGCAGCAGTC 3' | VH Amplification |
| 26 | 5' CAGGTCCAACTGCAGCAGCCT 3' | VH Amplification |
| 27 | 5' GAGGTGAAGCTGGTGGAGTC 3' | VH Amplification |
| 28 | 5' GATGTGAACTTGGAAGTGTC 3' | VH Amplification |
| 29 (gamma 1) | 5' TGGACAGGGATCCAGAGTTCCAGGTCACT 3' | VH Amplification |
| | FOR LIGHT CHAIN | |
| 30 | 5' GACATTGTGATGACCCAGTCT 3' | VL Amplification |
| 31 | 5' GATGTTTTGATGACCCAAACT 3' | VL Amplification |
| 32 | 5' GATATTGTGATAACCCAG 3' | VL Amplification |
| 33 | 5' GACATTGTGCTGACCCAATCT 3' | VL Amplification |
| 34 | 5' GATATTGTGCTAACTCAGTCT 3' | VL Amplification |
| 35 | 5' GATATCCAGATGACACAGACT 3' | VL Amplification |
| 36 | 5' GACATCCAGCTGACTCAGTCT 3' | VL Amplification |
| 37 | 5' CAAATTGTTCTCACCCAGTCT 3' | VL Amplification |
| 38 | 5'CAGGCTGTTGTGACTCAGGAA 3' | VL Amplification |
| 39 (kappa 18) | 5' TACAGTTGGTGCAGCATC 3' | VL Amplification |

11.4. Sequencing of Light and Heavy Chains of Anti-PBP2a Monoclonal Antibody
Sequencing Steps:
I. Amplification This was performed using the previous starter sequences, defined by SEQ ID NO.: 18 to SEQ ID NO.: 39.

II. Sequencing

The device ABI Prism 3100, Genetic Analyser (Hitachi) was used.

11.5. Sequence Analysis and Identification of Light and Heavy Chain CDR

The obtained DNA sequences were analyzed with the aid of DNA Star program, and were translated to amino acid sequences (ExPASy site—Translate program) for later analysis by Kabat's (24) and Chotia's (25) algorithms for identification of light and heavy chain CDRs.

12. Determination of Association and Dissociation Constants for Monoclonal Antibodies (Clones 10 and 38 by Surface Plasmon Resonance [SPR] [Biacore] Method)

SPR measurements were performed using a CM-5 sensor in a Biacore X® (Biacore AB, Uppsala, Sweden) device. Binding reagents and HBS-EP buffers (10 mM hepes, 150 mM NaCl, 3 mM EDTA, 0.005% P20[ Tween 0, pH 7.4]) were acquired with the company GE Healthcare.

Example 2

1. Obtainment of Murine Anti-PBP2a Monoclonal Antibodies:

A group of animals was subjected to the immunization protocol according to what was previously described. The result evaluated by ELISA test is described in FIG. 1.

After the fusion process (fusion of number 90-LATAM), the supernatant from 96 cavities (hybridomas) was analyzed by ELISA test. From this total, the five best samples were selected and the cells were expanded (cloning). Then, again, the resulting supernatants were analyzed by ELISA. Positive samples were validated by immunoblotting against the purified recombinant protein (PBP2a) for validating the results obtained by ELISA. The final result is in Table I.

Figure 1:
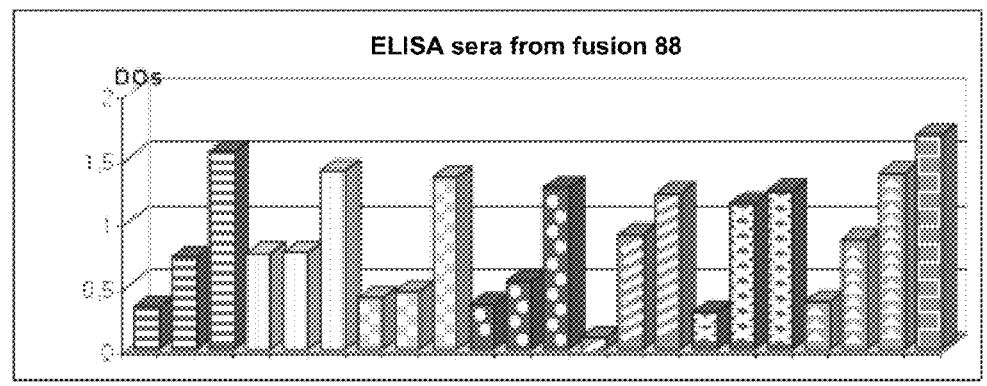
FIG. 1 shows the immunoenzyme test (ELISA) of sera of animals immunized for producing anti-PBP2a antibodies.

FIG. 1 reveals the result from the immunoenzyme test (ELISA) of the sera of the immunized animals for producing anti-PBP2a antibodies. Each dashing corresponds to the 1:100 diluted serum of the immunized animals. Positive control serum is in angular dashing [⊓⊔⊓⊔]. First bar of each dashing: pre-immune serum; second bar: serum after fourth immunization; and third bar: serum after fifth immunization.

TABLE I

Clonings of fusion 90: final balance

| Cloned hybridomas | Total number of clones | Positive clones (ELISA) | Positive clones (immunoblotting) | Selected clones |
|---|---|---|---|---|
| 77 | 70 | 2 | 1 (clone 38) | 1 |
| 68 | 108 | 10 | 1 (clone 10) | 1 |
| 79 | 91 | Zero | — | — |
| 17 | 101 | Zero | — | — |
| 70 | 48 | 2 | Zero | — |
| | 418 | 14 | 2 | 2 |

From the selected clones, clone 77-38 was subjected to recloning process for verifying the cell stability for secreting monoclonal antibodies. From the 50 analyzed cavities, all presented positive result by ELISA test. These clone were expanded and are stocked in liquid nitrogen at LATAM (Laboratory of monoclonal antibody technology) facilities.

2. Growth, Production, and Purification of Monoclonal Antibodies:

The process was standardized according to what was previously described. The obtained output is approximately 4 milligrams of monoclonal antibody for every 100 mL of supernatant subjected to the purification process. The obtained results can be seen below.

Figure 2:
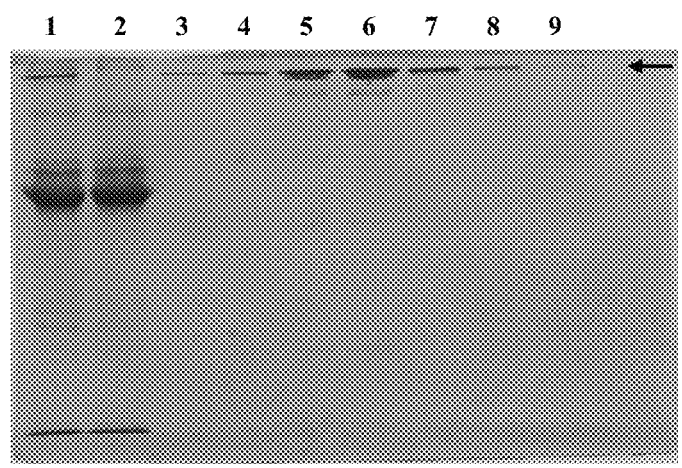
FIG. 2 shows the result of a polyacrylamide gel with raw samples and samples after purification.

In FIG. 2, we can see a polyacrylamide gel with raw samples and after purification. This FIG. 2 shows the non-denaturing polyacrylamide gel with supernatant samples before (column 1) and after purification (2) in HPLC column with MAb SelectSure resin. Columns 3 to 9 correspond to obtained purified sample fractions. The arrow indicates the approximate size of 150 kDa.

3. Functional Characterization of Monoclonal Antibodies:

3.1. In Vitro PBP2a Recognition—Immunoblotting

In order to investigate the capacity for antibody recognition by the target in the pathogen (PBP2a and similar sequences), the immunoblotting test was performed with bacteria presenting PBP2a (CEB and COL MRSA), a MSSA (methicillin-sensitive *Staphylococcus aureus*) strain (not presenting PBP2a), a vancomycin-resistant *Enterococcus* sp. strain (presenting PBP5), a transpeptidase with low-affinity for beta-lactam antibiotics (homologous to PBP2a), and an *Escherichia coli* strain (where the recombinant protein was generated) as negative control. The obtained results show that the antibody was able to recognize a protein with molecular weight of approximately 76 kDa in MRSA and *Enterococcus* sp. strains, corresponding to the size of PBP2a and PBP5, respectively. No reactivity of the monoclonal antibody was seen with proteins of methicillin-sensitive *Staphylococcus aureus* (PBP2a-negative) neither with *Escherichia coli* strain. The results can be seen in FIG. 3 (immunoblotting against MRSA and MSSA).

Figure 3:
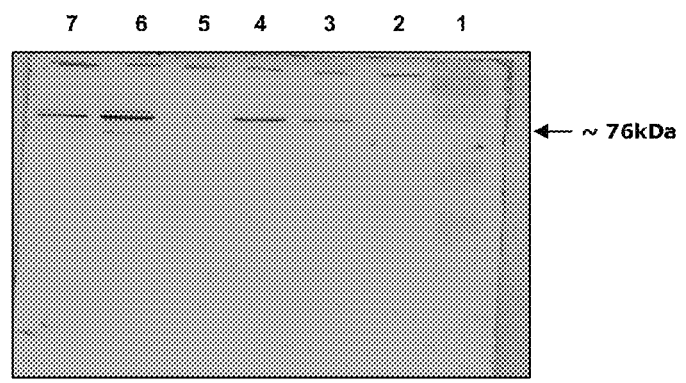
FIG. 3 shows the immunoblotting test of MRSA and MSSA lysates against a supernatant containing anti-PBP2a monoclonal antibodies.

The result of the immunoblotting test of MRSA and MSSA lysates against the supernatant containing anti-PBP2a monoclonal antibodies is shown in FIG. 3.
1.—molecular weight marker (Kaleidoscope);
2.—MSSA sample grown in exponential phase;
3 and 4.—MRSA sample grown in exponential phase;
5.—MSSA sample grown in stationary phase (overnight); and
6 and 7.—MRSA samples grown in stationary phase. The left arrow indicates PBP2a molecular weight.

3.2. PBP2a Recognition on the Bacterium Surface—Flow Cytometry

The objective of the flow cytometry test is to validate the capacity for target recognition on the bacterium in its native form by the monoclonal antibody. In previous tests (immunoblotting), we observed the target recognition on proteins subjected to a denaturation process, which occurs during the protein separation by electrophoresis in denaturing polyacrylamide gel. Again, we analyze a negative control strain (MSSA, PBP2a-negative) and a MRSA strain (CEB) grown in exponential and stationary phases. The obtained results show that the antibody is able to recognize the target on the bacterial surface in both conditions. The presence of protein A on *Staphylococcus* surface was not able to inhibit the antibody binding with PBP2a. The obtained results can be seen in FIG. 4.

Figure 4:
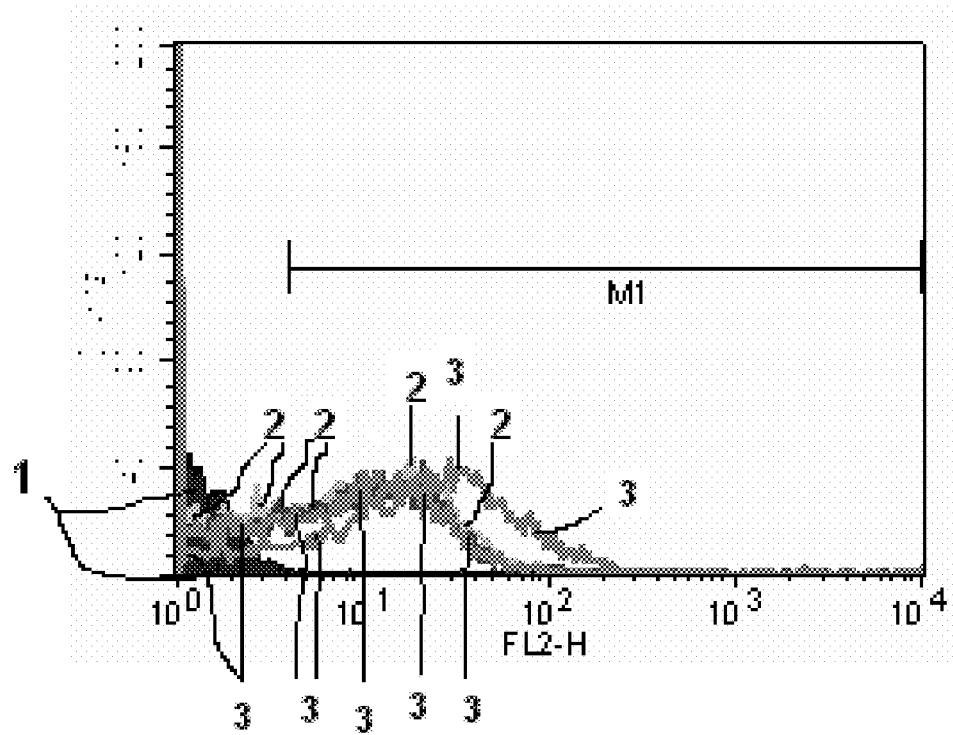
FIG. 4 is a representation of flow cytometry results of MRSA (CEB) and MSSA bacteria, incubated with anti-PBP2a monoclonal antibody and marked with phycoerythrin (PE).

FIG. 4 shows the results of the flow cytometry of MRSA (CEB) and MSSA bacteria incubated with anti-PBP2a monoclonal antibody and marked with phycoerythrin (PE). In (1), MSSA bacteria; in (2), MRSA grown in stationary phase; in (3), MRSA grown in exponential phase. MRSA populations present a right shift, corresponding to an increase in marked cells by the fluorescent conjugate.

4. Evaluation of Protection Conferred by Anti-PBP2a Monoclonal Antibody:

4.1. In Vitro Protection Tests
Determination of Minimum Inhibitory Concentration (MIC)

These assays aim to evaluate the antibody capacity for directly binding itself to the target in a closed system. For monoclonal antibodies with therapeutic finality, positive results have extreme significance, as they mean that the antibody is able to recognize the target and to block the bacterial growth without the aid of the host immune system, such as complement activation and opsonization mechanisms, resulting from the combined action with the innate and adaptive immune system of the host. CEB, COL, and Iberian MRSA strains were evaluated, where similar MIC values (approximately 500 micrograms) were seen in the evaluated conditions. These data indicate that regardless of the genetic background of the different MRSA strains, the antibody doses needed for blocking the growth are not the same. These results can be seen in FIG. 5.

Figure 5:
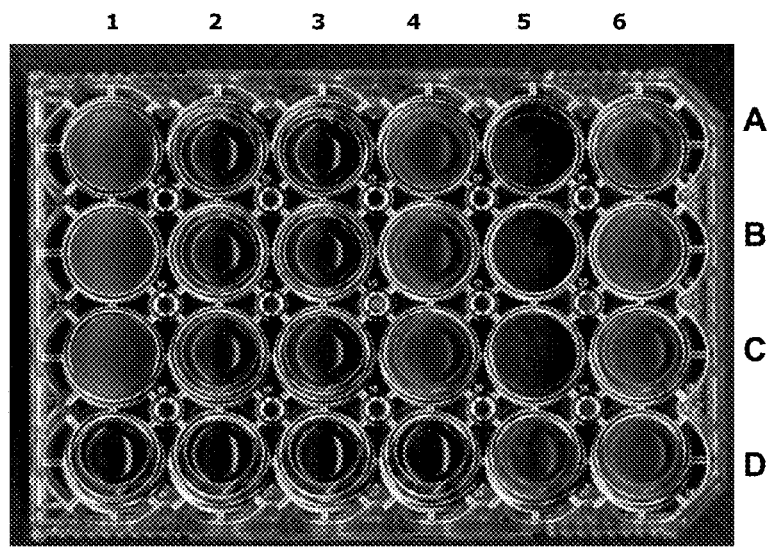
FIG. 5 shows the in vitro protection test (MIC—minimum inhibitory concentration) conferred by anti-PBP2a purified monoclonal antibody and vancomycin against an inoculum of different MRSA strains.

FIG. 5 shows the test of the in vitro protection (MIC—minimum inhibitory concentration) conferred by anti-PBP2a purified monoclonal antibody and vancomycin against an inoculum of $10^5$ cells from different MRSA strains. An absence of turbidity indicates that there was no bacterial growth in the analyzed conditions.
1A: CEB MRSA (Brazilian epidemic clone)+250 μg of antibody;
2A: CEB MRSA+500 μg of antibody;
3A: CEB MRSA+750 μg of antibody;
4A and 6A: negative controls of CEB MRSA strain.
1B: COL MRSA+250 μg of antibody;
2B: COL MRSA+500 μg of antibody;
3B: COL MRSA+750 μg of antibody;
4B and 6B: negative controls of COL MRSA strain.
1C: Iberian MRSA (European epidemic clone—EEC)+250 μg of antibody;
2C: EEC MRSA+500 μg of antibody;
3C: EEC MRSA+750 μg of antibody;
4C and 6C: negative controls of EEC MRSA strain.
1D: CEB MRSA+150 μg of vancomycin;
2D: CEB MRSA+300 μg of vancomycin;
3D: CEB MRSA+500 μg of vancomycin;
4D: CEB MRSA+750 μg of vancomycin;
5D and 6D: negative controls.
4.2. In Vivo Protection Tests
4.2.1. Determination of Lethal and Sublethal Doses for CEB, Iberian, WB79 CA, and COL MRSA Strains:

These assays were necessary in order that the in vivo protection was evaluated in the two used models—the renal quantification by sublethal dose one and the survival test after systemic infection with a larger inoculum of bacteria—able to cause death in about 50% of the animals ($LD_{50}$). The chosen route was intraperitoneal, due to the administration facility and the absence of losses. An adaptation of Reed-Muench method was used for conducting the assay, with two animals per condition (infective bacterial dose in growing concentrations) for determining $LD_{50}$ and sublethal doses, and three different doses were tested, once we had previous knowledge on the mean lethal doses for *Staphylococcus aureus*. COL MRSA strain, the first MRSA clone to have its genome sequenced, is used as reference strain for studies on this pathogen. However, it showed to be little virulent, needing high infective doses in relation to the other MRSA clones to cause infection in animals. Therefore, it was not used in protection assays.

4.2.2. Renal Protection Assays after Systemic Infection with Sublethal Dose

Using a renal quantification model after infection, these assays enable to evaluate the antibody capacity to reduce the presence of bacteria in vital organs (kidneys) after a systemic infection. A reduction higher than 3 log (1000 times) was reached in three independent assays with virulent MRSA strains from different genetic backgrounds. In these assays, the animals received a previous dose of 500 micrograms of antibody. The protection conferred by a lower antibody dose (250 micrograms) was evaluated in the assay with CA-MRSA strain, where a bacterial reduction was also observed, but lower than the one obtained with the 500-microgram dose. The results can be seen in FIGS. 6A, 6B, and 6C.

Figure 6A:
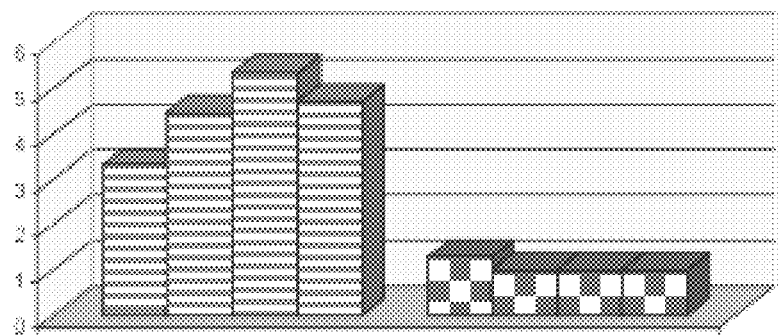
FIG. 6A shows renal quantification results in treated and non-treated animals with the anti-PBP2a monoclonal antibody, subjected to systemic infection with a sublethal dose of MRSA CEB strain.

FIG. 6A shows the results of renal quantification in animals treated and non-treated with anti-PBP2a monoclonal antibody and subjected to systemic infection with a sublethal dose of MRSA CEB strain. In horizontal stripes: log of concentration of bacteria isolated from the kidneys of each non-treated animal. In checkered pattern: log of quantity of bacteria isolated from the kidneys of each animal treated with the antibody. Bacterial quantification: controls: C1: 2000 bacteria; C2: 29,000 bacteria; C3: 220,000 bacteria; C4: 52,000 bacteria (mean of 75,750 bacteria). Treated (protected) animals: P1: 20 bacteria; P2, P3, and P4: 10 bacteria (mean of 12.5 bacteria). Reduction in the quantity of bacteria recovered from treated animals in relation to non-treated ones: 6060 times.

Figure 6B:
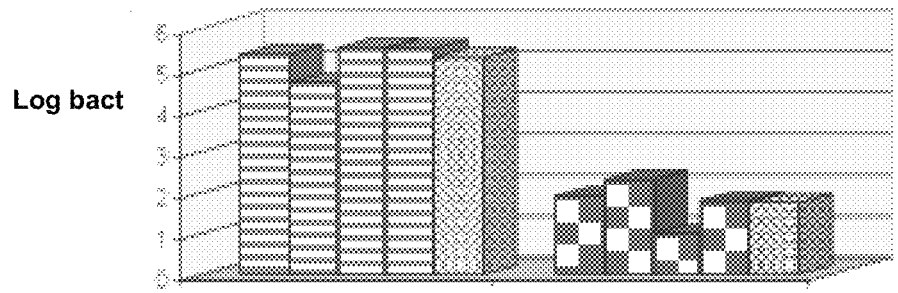
FIG. 6B shows renal quantification results in treated and non-treated animals with the anti-PBP2a monoclonal antibody, subjected to systemic infection with a sublethal dose of MRSA Iberian strain (European epidemic clone).

FIG. 6B shows the results of renal quantification in animals treated and non-treated with anti-PBP2a monoclonal antibody and subjected to systemic infection with a sublethal dose of Iberian MRSA strain (European epidemic clone). In horizontal stripes: log of concentration of bacteria isolated from the kidneys of each non-treated animal. In large checkered pattern: log of quantity of bacteria isolated from the kidneys of each animal treated with the antibody. Bars in small checkered pattern indicate the respective obtained means. Bacterial quantification: controls: C1: 210,000 bacteria; C2: 44,000 bacteria; C3: 300,000 bacteria; C4: 290,000 bacteria (mean of 211,000 bacteria). Treated (protected) animals: P1: 80 bacteria; P2: 200 bacteria; P3: 10 bacteria; and P4: 60 bacteria (mean of 87.5 bacteria). Reduction in quantity of bacteria recovered from treated animals in relation to the non-treated ones: 2420 times.

Figure 6C:
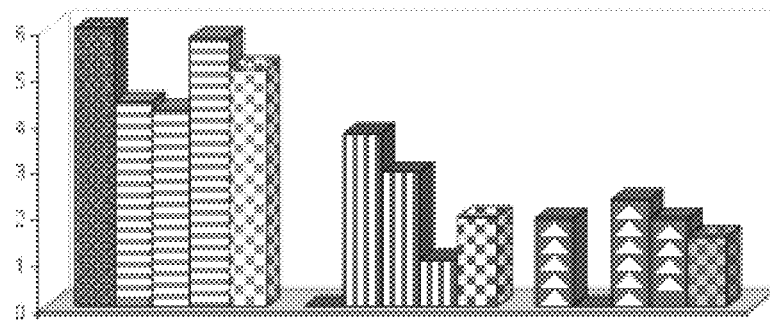
FIG. 6C shows renal quantification results in treated and non-treated animals with the anti-PBP2a monoclonal antibody, subjected to systemic infection with a sublethal dose of WB79 CA-MRSA strain (Brazilian community strain).

FIG. 6C shows the results of renal quantification in animals treated and non-treated with anti-PBP2a monoclonal antibody and subjected to systemic infection with a sublethal dose of WB79 CA-MRSA strain (Brazilian community strain). Five first bars (in xx, horizontal dashing, and large checkered pattern): log of concentration of bacteria isolated from the kidneys of each non-treated animal. First bar (in xx): estimate in relation to an animal killed before the euthanasia. Bars 6, 7, 8, and 9 (in horizontal dashing and checkered pattern): log of quantity of bacteria isolated from the kidneys of animals treated with 250 µg of anti-PBP2a monoclonal antibody. Bars 10, 11, 12, and 13 (in triangles): log of quantity of bacteria isolated from the kidneys of each animal treated with 500 µg of antibody. Checkered bars ($5^{th}9^{th}$, and $13^{th}$ bars) indicate the respective obtained means. Bacterial quantification: controls: C1: 650,000 bacteria; C2: 26,000 bacteria; C3: 17,000 bacteria; C4: 500,000 bacteria (dead animal estimate) (mean of 231,000 bacteria). Animals treated with 250 µg of antibody: P1: zero; P2: 5,400 bacteria; P3: 830 bacteria; and P4: 10 bacteria (mean of 1,560 bacteria). Animals treated with 500 µg of antibody: P1: 80; P2: zero; P3: 210; P4: 80 bacteria (mean of 92.5), Reduction in quantity of bacteria recovered from treated animals in relation to the ones non-treated with 250 µg of antibody: 149 times. With 500 µg: 2,497 times.

4.2.3. Survival Assays

In this assay type, we evaluate the protection conferred by the antibody to animals after an infection with a bacterial load able to kill 50% of the animals ($LD_{50}$) or more. The protection against the three strains used in the renal quantification assay was evaluated. A significant reduction in (i) survival time and (ii) the very survival of animals under treatment with anti-MRSA monoclonal antibodies was observed in the three independent assays.

In the assay with CEB MRSA strain, 70% of the animals under treatment survived the infection, against only 10% of the control group (non-treated). In the assay with Iberian MRSA strain, the obtained results were similar, with 60% of protection in animals under treatment and 100% of death in control group. In the assay with CA MRSA strain, a protection of 100% was seen, compared to 70% in control animals. These results can be seen in FIGS. 7a, 7b, and 7c.

Figure 7A:
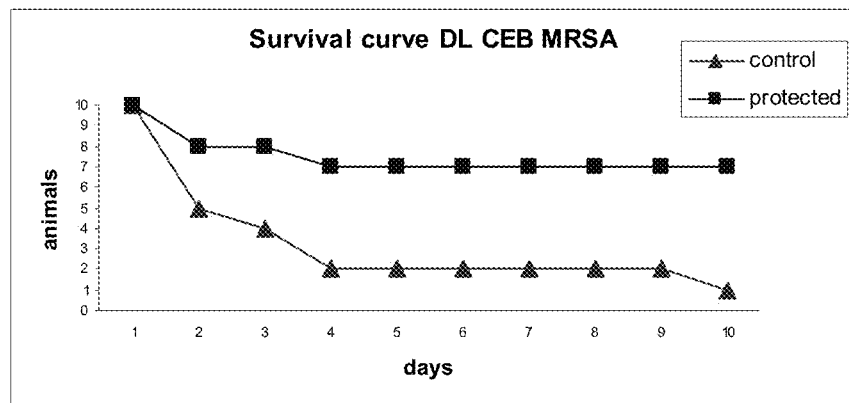
FIG. 7A shows the survival curve of treated (protected) and non-treated (control) animals after infection by a lethal bacterial dose (MRSA CEB).

FIG. 7A shows the survival curve of treated (protected) and non-treated (control) animals after infection by a dose of $2.3 \times 10^8$ bacteria (CEB MRSA) administered by intraperitoneal route ($LD_{50}$).

Figure 7B:
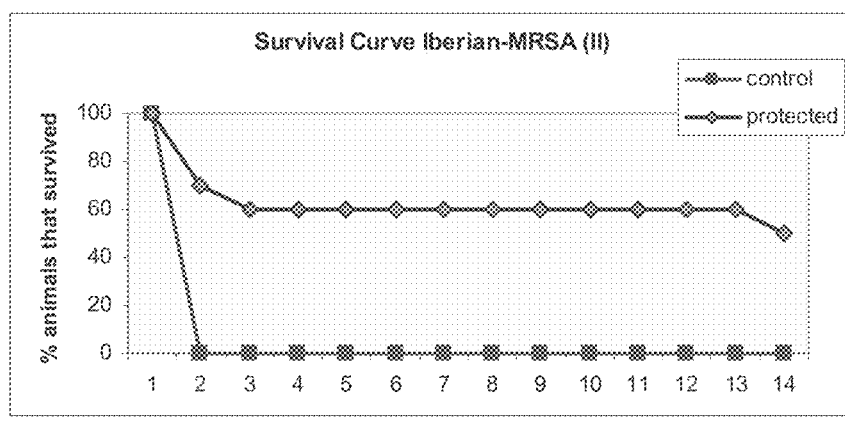
FIG. 7B shows the survival curve of treated (protected) and non-treated (control) animals after infection by a lethal bacterial dose (Iberian MRSA).

FIG. 7B shows the survival curve of treated (protected) and non-treated (control) animals after infection by a dose of $4.2 \times 10^8$ bacteria (Iberian MRSA) administered by intraperitoneal route (~$LD_{50}$).

Figure 7C:
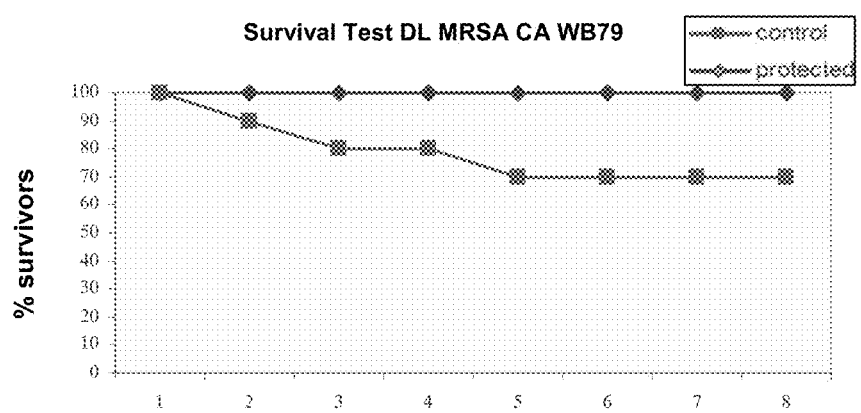
FIG. 7C shows the survival curve of treated (protected) and non-treated (control) animals after infection by a lethal bacterial dose (WB79 CA-MRSA).

FIG. 7C shows the survival curve of treated (protected) and non-treated (control) animals after infection by a dose of $1.1 \times 10^9$ bacteria (WB79 CA-MRSA) administered by intraperitoneal route (~$LD_{50}$).

4.2.4. Comparative Study on Protection Conferred by Monoclonal Antibody Versus Vancomycin As vancomycin is a first choice antimicrobial for treatment of severe infections by MRSA, a comparative study on protection was conducted in a model different from the previous ones. In this study, the animals were infected and the administration of the antimicrobial or monoclonal antibodies was started just after four hours of infection. The study was conducted with three distinct groups: one treated with vancomycin, other treated with monoclonal antibodies, and a third one with simultaneous administration of antimicrobial+antibodies. Vancomycin doses were adjusted and administered in a way similar to the cases of infections in humans (500 mg every 12 hours).

The obtained results indicated that there was a reduction of around 15 times in the quantity of bacteria present in the kidneys of animals treated with antimicrobial or antibodies three days after the infection. However, a reduction of 4,617 times was seen in the group that received treatment with antimicrobial and antibodies.

Based on these results, we can conclude that the protection conferred by an antibody dose corresponded to five vancomycin doses and that the simultaneous administration of vancomycin and antibodies was very efficient in reducing the bacterial load observed in the kidneys of infected animals. This study was repeated with a little lower infective dose in order that we could better observe the protective action of anti-MRSA monoclonal antibodies both isolated and in association with vancomycin (See FIG. 8).

After the conduction of the second assay with a lower infective dose, the obtained results confirmed the initial results. The protection conferred by the treatment with monoclonal antibody caused a reduction of 89 times, which was higher than the protection obtained with the treatment with 5 vancomycin doses (reduction of 35 times). However, the most significant reduction result was seen in the group treated with antibody+vancomycin, causing a reduction of 450 times.

Figure 8A:
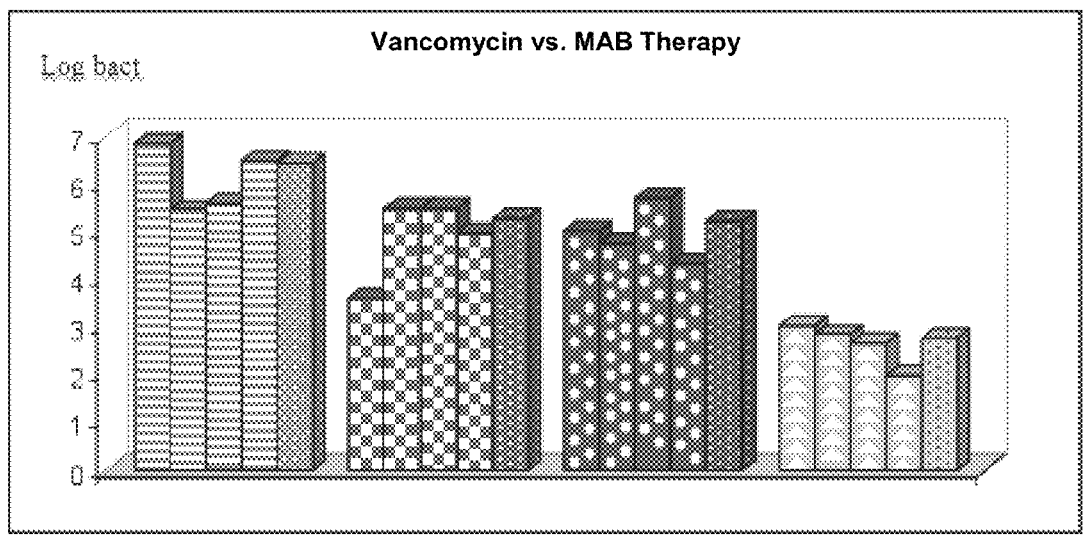
FIG. 8A shows the bacterial quantification in kidneys of animals treated with anti-PBP2a monoclonal antibody, vancomycin, and antibody+vancomycin association and non-treated animals after infection with bacteria (MRSA CEB).

FIG. 8A shows the bacterial quantification in kidneys of animals treated with anti-PBP2a monoclonal antibody, vancomycin, and association of antibody+vancomycin and in non-treated animals after infection with $6.0 \times 10^7$ bacteria (CEB MRSA). The treatment beginning happened 4 hours after the infection. Vancomycin was administered every 12 hours (5 doses). Bars 1, 2, 3, 4, and 5 (dashing): log of concentration of bacteria recovered from non-treated animals (controls). C1: 7,000,000; C2: 295,000; C3: 380,000; C4: 3,200,000 (mean: 2,718,750 bacteria). Bars 6, 7, 8, 9, and 10 (checkered pattern): log of concentration of bacteria recovered from animals treated with 400 μg of anti-PBP2a monoclonal antibody. P1: 4,200; P2: 310,000; P3: 330,000; P4: 90,000 (mean of 183,550 bacteria). Bars 11, 12, 13, 14, and 15 (spheres): animals treated with vancomycin. P1: 110,000; P2: 58,000; P3: 500,000; P4: 21,000 (mean of 172,250 bacteria). Bars 16, 17, 18, 19, and 290. (triangles): log of concentration of bacteria recovered from animals treated with antibody (300 μg)+vancomycin. P1: 1,100; P2: 700; P3: 450; P4: 90 (mean of 585 bacteria).

Figure 8B:
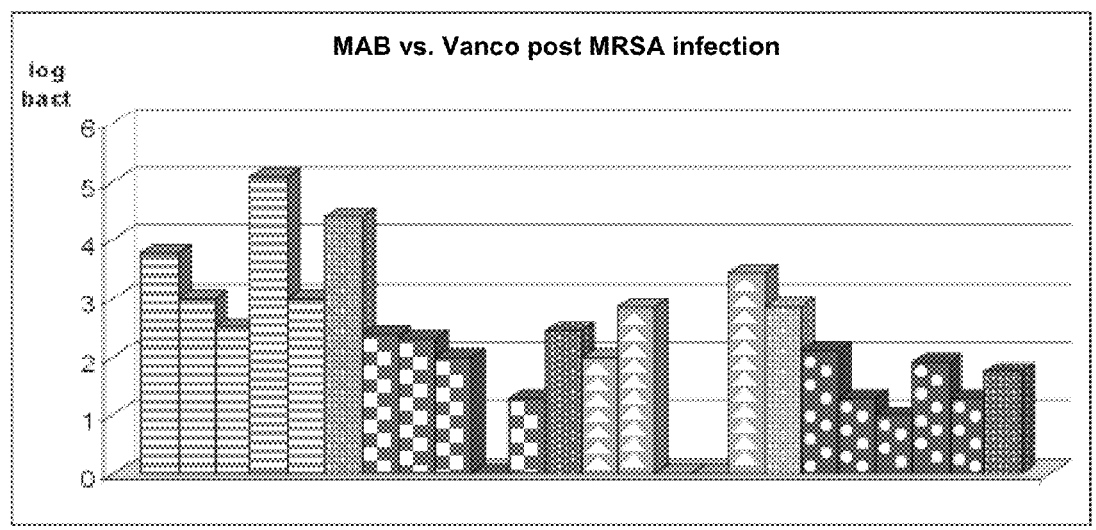
FIG. 8B shows the bacterial quantification in kidneys of animals treated with anti-PBP2a monoclonal antibody.

FIG. 8B shows the bacterial quantification in kidneys of animals treated with anti-PBP2a monoclonal antibody (bars 7 to 12), vancomycin (bars 13 to 18), antibody+vancomycin association (19 to 24) and of non-treated animals (bars 1 to 6) after infection with $7.0 \times 10^6$ bacteria (CEB MRSA). Treatment beginning in 4 hours after infection. Vancomycin administered every 12 hours (5 doses). Bars 1 to 6: log of concentration of bacteria recovered from non-treated animals (controls). C1: 6,000; C2: 1,000; C3: 500; C4: 118,000; and C5: 1,000 (mean: 25,220 bacteria). Bars 7 to 12: log of concentration of bacteria recovered from animals treated with 500 μg of anti-PBP2a monoclonal antibody. MB1: 450; MB2: 200; MB3: 100; MB4: 20; MB5: zero (mean of 284 bacteria). Bars 13 to 18: animals treated with vancomycin. VC1: 100; VC2: 700; VC3: zero; VC4: zero; VC5: 2800 (mean of 720 bacteria). Bars 19 to 24: log of concentration of bacteria recovered from animals treated with antibody (500 μg)+vancomycin. MBV1: 130; MBV2: 20; MBV3: 10; MBV4: 80; MBV5: 20 (mean of 56 bacteria).

5. Avidity Assays

Results of the avidity tests of monoclonal antibodies clones 10 and 38:
Urea Protocol Avidity:
clone 10: 1.03/1.46 (reading DOs with/without treatment)= 70.5%
clone 38: 1.00/1.21=82.6%
Ammonium Thiocyanate Protocol Avidity:
Clone 10 (DOs):
Control: 1.12
Thiocyanate-Treated Samples:
2 M=0.046; 1.5 M=0.047; 1 M=0.107; 0.75 M=0.483; 0.5 M=0.602; 0.375 M=0.684
Avidity rate: 2.47
Clone 38 (DOs):
Control: 1.22
Thiocyanate-Treated Samples:
2 M=0.056; 1.5 M=0.062; 1 M=0.129; 0.75 M=0.648; 0.5 M=0.758; 0.375 M=0.793
Avidity rate: 4.40

It is seen that the avidity rates of clone 38 were higher than the ones of clone 10 in both assays. Furthermore, it is verified that, according to both protocols, it was necessary to use 50 times more antibody from clone 10 than from clone 38 in order to reach a DO close to 1.0.

6. Determination of Association and Dissociation Constants of the Monoclonal Antibodies (Clones 10 and 38 by Surface Plasmon Resonance Method [SPR] [Biacore])

The results obtained by SPR method confirmed the preliminary results of antibody avidity, where clone 38 showed results higher than the ones of clone 10 again. According to the data seen in Table II, we see that clone 38 shows affinity 450 times higher than the clone 10 one.

This affinity is mainly due to its higher association rate, which is about 100 times higher than the clone 10 one. Due to the very high affinity of clone 38, its measures present parameters close to the equipment detection threshold. Yet, due to the care in trial planning and conduction, we obtained an excellent adjustment for trial data using Langmuir's model, which indicates that the obtained data are reliable.

Figure 9A:
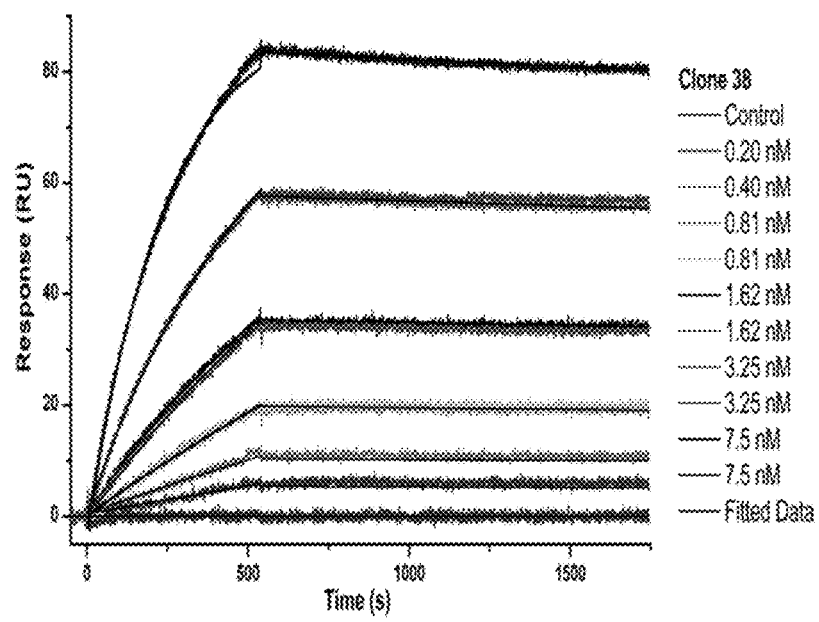
FIG. 9 show the interaction between recombining PBP2a (antigen) and monoclonal antibodies clone 38 (FIG. 9A) and clone 10 (FIG. 9B).
Figure 9B:
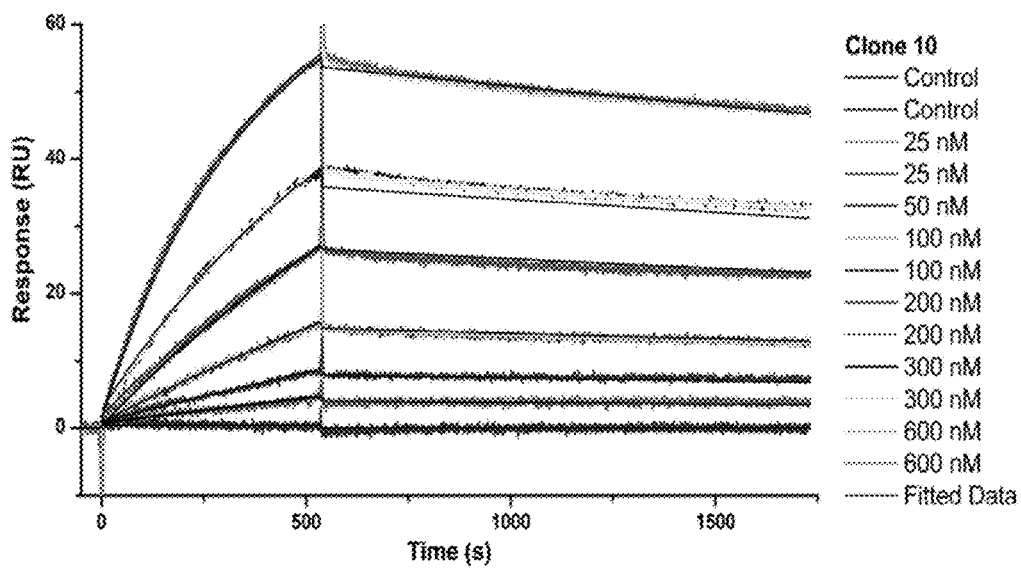

FIG. 9 shows the interaction between recombinant PBP2a (antigen) and monoclonal antibodies clone 38 (FIG. 9A) and clone 10 (FIG. 9B). Smoky dashing curves represent SPR data in the concentrations according to the right key. All samples were analyzed in duplicate, and the 1:1 Langmuir's theoretical model for each curve is shown in black under each curve. Response units are represented in the vertical axis, and time is represented in the horizontal line in seconds. The closest lines referring to the horizontal axis represent the baseline for each sample (negative control).

TABLE II

Dissociation and interaction constants between antigen (PBP2a) and monoclonal antibodies clones 10 and 38.

|  | $k_a$ (M$^{-1}$s$^{-1}$) | $k_d$ (s$^{-1}$) | $K_D$ (nM) |
|---|---|---|---|
| Clone 10 | $4.42 \times 10^3 \pm 5.7$ | $1.16 \times 10^{-4} \pm 5.63 \times 10^{-7}$ | 26.2 |
| Clone 38 | $5.45 \times 10^5 \pm 384$ | $3.13 \times 10^{-5} \pm 2.11 \times 10^{-10}$ | $5.7 \times 10^{-2}$ |

7. Identification of Complementary-Determining Regions (CDRs) of Light and Heavy Chains of Anti-PBP2a Monoclonal Antibody After the mRNA extraction process in the hybridoma cells of the clone producing the used antibodies (clone 38), cDNA obtainment was performed and PCR reactions were performed with this material for different light and heavy chain alleles. The obtained materials were subjected to sequencing using the same starter sequences (defined by SEQ ID NO.: 18 to SEQ ID NO.: 39) used in PCR reactions. Light chain 391 and heavy chain 310 were identified in three distinct sequencings. Applying the Kabat's and Chotia's algorithms, we obtain the identification of light and heavy chain CDRs, which are the target of the attached claims.

We present the sequences of light and heavy chain CDRs below.

SEQ ID NO.: 6-CDR 1 light chain amino acids.
RSSQSIGHSNGNTYLE

SEQ ID NO.: 7-CDR 2 light chain amino acids.
KVSNRFS

-continued

SEQ ID NO.: 8-CDR 3 light chain amino acids.
FQGSYVPLT

SEQ ID NO.: 9-CDR 1 light chain DNA.
cgcagcagccagagcattggccatagcaacggcaacacctatctggaa SEQ ID NO.: 10-CDR 2 light chain DNA.
aaagtgagcaaccgctttagc SEQ ID NO.: 11-CDR 3 light chain DNA.
tttcagggcagctatgtgccgctgacc SEQ ID NO.: 12-CDR 1 heavy chain amino acids.
GFSITSSSSCWH

SEQ ID NO.: 13-CDR 2 heavy chain amino acids.
RICYEGSISYSPSLKS

SEQ ID NO.: 14-CDR 3 heavy chain amino acids.
ENHDWFFDV

SEQ ID NO.: 15-CDR 1 heavy chain DNA.
ggctttagcattaccagcagcagcagctgctggcat

SEQ ID NO.: 16-CDR 2 heavy chain DNA.
cgcatttgctatgaaggcagcattagctatagcccgagcctgaaaagc SEQ ID NO.: 17-CDR 3 heavy chain DNA.
gaaaaccatgattggttttttgatgtg Complementary Data Further other assays were conducted, proceeding the invention development. These are reported below, through examples.

Example 3

A second study using CEB MRSA strain was conducted, following the same protocol described in Example 1, item 7.2, with adding of two pulses of agitation by vortex, of 15 seconds each one, after each washing; aiming to disaggregate *Staphylococcus aureus* agglomerates and to increase the quantity of PBP2a exposed to antibodies.

The markers FITC (fluorescein isothiocyanate) and PE (phycoerythrin) were tested, with control samples (i. pure bacterium, without contact with monoclonal antibody; and ii. pure bacterium plus FITC or PE marker) and the sample treated with monoclonal antibody and subjected to marking with PE or FITC being analyzed. The readings in FACsalibur device were performed in linear mode.

Figure 10:
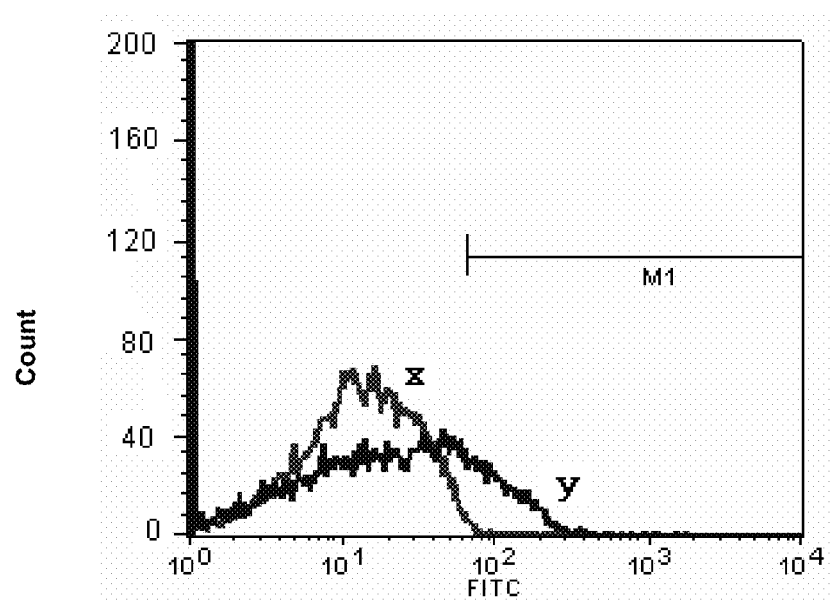
FIG. 10 is a graph of the second analysis by flow cytometry of MRSA samples in presence of FITC-marked anti-PBP2a antibody.

FIG. 10 is a graph of analysis by flow cytometry of MRSA samples in presence of FITC-marked anti-PBP2a antibody. Curve (x) corresponds to non-marked sample, and curve (y) corresponds to marked sample.

The obtained results showed that about 22% of marked population was detected by the device, confirming the recognition of the target (PBP2a) present on the bacterial surface by anti-PBP2a antibodies (FIG. 10).

Example 4

The inventors still surveyed the protection conferred by anti-PBP2a monoclonal antibody from methicillin-resistant *Staphylococcus aureus* against *enterococcus*.

According to what was already previously mentioned here, the antibody recognizes proteins present in *Enterococcus* sp. strains, probably PBP5—a transpeptidase with low affinity for beta-lactams, present in all *enterococcus* strains, with molecular weight of approximately 76 kDa (237 amino acids). This enzyme presents homology referring to PBP2a of MRSA, according to alignment (ClustalW) related below:

```
PBP5Efas    MERSNRNKKSSKNPLILGVSALVLIAAAVGGYYAYSQWQAKQELAEAKKTATTFLNVLSK    60
PBP5efam    -----KHGKNRTGAYIAG--AVILIAAAGGGYFYYQHYQETQAVEAGEKTVEQFVQALNK    53
PBP2a       ------------MKKIKIVPLILIVVVVGFGIYFYASKDKEINNTIDAIEDKNFKQVYKD    48
                         *    :::::..  *.:*  :         *   :...

PBP5Efas    QEFDKLPSVVQEASLKKNGYDTKSVVEKYQAIYSGIQAEGVKASDVQVKKAKDNQYTFTY   120
PBP5efam    GDYNKAAEMTSKKAANKSALSEKEILDKYQNIYGAADVKGLQISNLKVDKKDDSTYSFSY   113
PBP2a       SSY-----------ISKSDNGEVEMTERPIKIYNSLGVKDINIQDRKIKKVSKNKKRVDA    97
               .:           .*.   .  .: ::  **..  .:.::.    :::.*  ...   .

PBP5Efas    KLSMSTPLGEMKDLSYQSSIAKKGDTYQIAWKPSLIFPDMSGNDKISIQVDNAKRGEIVD   180
PBP5efam    KAKMNTSLGELKDLSYKGTLDRNDGQTTINWQPNLVFPEMEGNDKVSLTTQEAARGNIID   173
PBP2a       QYKIKTNYGNIDRN-VQFNFVKEDGMWKLDWDHSVIIPGMQKDQSIHIENLKSERGKILD   156
             :  ...*  *::.       :  .: :...    : *.  .:::* *.  : ::  :    :: **:*:*

PBP5Efas    RNGSGLAINKVFDEVGVVPGKLGSGAEKTANIKAFSDKFGVSVDEIN---QKLSQGWVQA   237
PBP5efam    RNGEPLATTGKLKQLGVVPSKLGDGDEKTANIKAIASSFDLTEDAIN---QAISQSWVQP   230
PBP2a       RNNVELANTGTHMRLGIVPKNVS-----KKDYKAIAKELSISEDYINNKWIKIGYKMIPS   211
            **.  **   .   . :*:**  :::.       . :  **::..:.::  *  **       :.   :  .

PBP5Efas    DSFVPITVASEPVTELPTG--AATKDTESRYYPLGEACAINR-VYGTITAEDIEKN--PE   292
PBP5efam    DYFVPLKIIDGATPELPAG--ATIQEVDGRYYPLGEAAAQLIGYVGDITAEDIDKN--PE   286
PBP2a       FHFKIVKKMDEYLSDFAKKFHLTTNETESRNYPLEKATSHLLGYVGPINSEELKQKEYKG   271
             *  ..:.   .    .::..          : ::.:.* *** :*. :     *  *..:*::..:.

PBP5Efas    LSSTGVIGKTGLERAFDKELRGQDGGSLVILDDK-ENVKKALQTKEKKDGQTIKLTIDSG   351
PBP5efam    LSSNGKIGRSGLEMAFDKDLRGTTGGKLSITDAD-GVEKKVLIEHEVQNGKDIKLTIDAK   345
PBP2a       YKDDAVIGKKGLEKLYDKKLQHEDGYRVTIVDDNSNTIAHTLIEKKKKDGKDIQLTIDAK   331
            ... .**:.***   :**.*:       *  :  *  * .        ::.*    ::   ::*:  *:****:

PBP5Efas    VQQQAFAIFDKRPGSAVITDPQKGDLLATVSSPSYDPNKMANGISQKEYDAYNNNKDLPF   411
PBP5efam    AQKTAFDSLGGKAGSTVATTPKTGDLLALASSPSYDPNKMTNGISQEDYKSYEENPEQPF   405
PBP2a       VQKSIYNNMKNDYGSGTAIHPQTGELLALVSTPSYDVYPF<u>MYGMSNEEYNKLTEDKKEPL</u>   391
            .*:  :   :   :    **  .  *::.***  .:****    :  *.:*:::..*.     ::  .  *:

PBP5Efas    **TARFATGYAPG*STFK*IITGAIGLDAGTLKPDEELEINGLKWQKDKSWGGYFATR**VKEAS-   470
PBP5efam    **ISRFATGYAPG*STFK*MITAAIGLDNGTIDPNEVLTINGLKWQKDSSWGSYQVTR**VSDVS-   464
PBP2a       <u>LNKFQITTSPGSTQK</u>ILTAMIGLNNKTLDDKTSYKIDGKGWQKDKSWGGYNVTRYEVVNG   451
             :*       :****  *::.*.  ***: *:..  .         *:*  ****.***.*.**  ...
```

-continued

```
PBP5Efas   PVNLRTALVNSDNIYFAQQTLRMGEDKFRAGLNKFIFGEELDLPIAMTPAQISNEDKFNS   530
PBP5efam   QVDLKTALIYSDNIYTAQETLKMGEKKFRIGLDKFIFGEDLDLPISMNPAQISNEDSFNS   524
PBP2a      NIDLKQAIESSDNIFFARVALELGSKKFEKGMKKLGVGEDIPSDYPFYNAQISNKN-LDN   510
           ::*: *:   ****: *:  :*..:*..**. *:.*: .**::      .:  *****:: ::.

PBP5Efas   EILLADTGYGQGQLLISPIQQATMYSVFQNNGTLVYPKLVLDKETKK-KDNVISANAANT   589
PBP5efam   DILLADTGYGQGELLINPIQQAAMYSVFANNGTLVYPKLIADKETKD-KKNVIGETALQT   583
PBP2a      EILLADSGYGQGEILINPVQILSIYSALENNGNINAPHLLKDTKNKVWKKNIISKENINL   570
           :*****:*****::**.*:*   ::**.: ***.:  *:*: *.:.*  *.*:*.    :

PBP5Efas   IATDLLGSVEDPSGYVYNMYNPNFSLAAKTGTAEIKDKQDTDGKENSFLLTLDRSNNKFL   649
PBP5efam   IVPDLREVVQDVNGTAHSLSALGIPLAAKTGTAEIKEKQDVKGKENSFLFAFNPDNQGYM   643
PBP2a      LNDGMQQVVN--KTHKEDIYRSYANLIGKSGTAELKMKQGESGRQIGWFISYDKDNPNMM   628
           :  .:   *:  .  .:     *  .*;****:* **. .*::  .::::  : .*    :

PBP5Efas   TMIMVENSGENGSATDISKPLIDYLEATIK----------                      679
PBP5efam   MVSMLENKEDDDSATKRASELLQYLNQNYQ----------                      673
PBP2a      MAINVKDVQDKGMASYNAKISGKVYDELYENGNKKYDIDE                      668
           :::   :.. *:  :.  .   :    :
```

The alignment was performed with sequences corresponding to PBP5 from the enterococci *E. faecalis* (Efas) and *E. faecium* (Efam) with MRSA PBP2a. Marked sequences (bold—PBP5; underlined—PBP2a) correspond to the used PBP2a region to generate monoclonal antibodies. Amino acids corresponding to the enzyme active core are marked in italic.

Thus, in vitro protection assays, determination of lethal dose and $LD_{50}$, and in vivo assays (sublethal dose with renal quantification and survival assay with lethal dose) with an *enterococcus* strain, in murine model (Balb/C mice) were conducted, as previously conducted with MRSA. These results can be seen in the corresponding reports.

1.1. In Vitro Protection Assays

The objective of this assay was to evaluate the in vitro protection conferred by the antibody against VRE *enterococcus* strain.

In vitro protection test (MIC), clone 38 purified monoclonal antibody (90/DA5/CB5/AA3 hib 77) against *Enterococcus f.* clinical strain (VRE), Richet laboratory.

Figure 11:
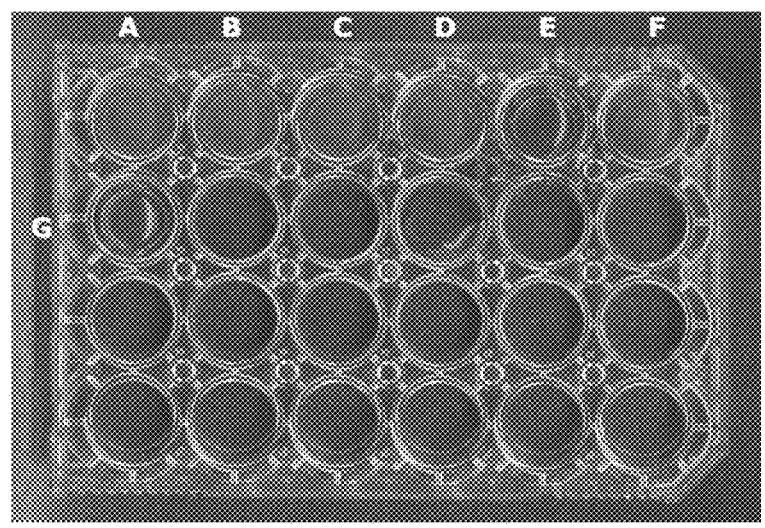
FIG. 11 shows the result of the in vitro protection conferred by the antibody against VRE *enterococcus* strain.

Conditions:
Sample: purified from supernatant by HPLC, SelecSure MAB resin, dialysed, lyophilized.
Antibody quantification (Lowry's method): 3.5 mg/mL
Inoculum: VRE strain
Pre-inoculum: 1 VRE colony in 20 mL Lb and vancomycin (10 mg/mL), ON 37° C., 160 rpm
Inoculum: 400 mL of pre-inoculum in 20 mL Lb, 200-mL erlenmayer, 37° C., 160 rpm
$DO_{600nm}$ reading after 7 hours: 0.7
Quantification: $5.5 \times 10^8$ bacteria/mL
Test Conditions:
Inoculum: $5.5 \times 10^5$ bacteria
Antibody concentrations: 300, 400, 500, 600, and 700 mg of antibody
Culture medium: 1 mL of Luria broth
Cell culture plate, 24 cavities
Positive control: Luria broth+bacterial inoculum
Negative control: Luria broth
Incubation: 18 hours, 37° C.
FIG. 11 shows the result of the evaluation of the protection conferred by the antibody. In FIG. 11, we have:
A. 300 mg of antibody
B. 400 mg of antibody
C. 500 mg of antibody
D. 600 mg of antibody
E. Negative control
F. Positive control
G. 700 mg of antibody 1.2. $LD_{50}$ and Lethal Dose Determination by Intraperitoneal Route—Vancomycin-Resistant *Enterococcus Faecium*

Protocol:
Female 7-week Balb/C animals, mean weight of 20 grams
Day 01—pre-inoculum: 1 VRE strain colony in 10 mL of Lb broth and vancomycin (10 mg/mL), 50-mL Falkow tube, growth ON 37° C., 160 rpm
Day 02—inoculum: 1 mL of pre-inoculum in 50 mL of Lb broth/vancomycin (250-mL erlenmayer)—4 vials, 37° C., 160 rpm, growth until $OD_{600nm}=0.80$
centrifugation for 10 min, 4000 rpm, resuspension in PBS 1× sterile, OD 1.2
Quantification: $2.1 \times 10^8$ bacteria/mL
A. 60 microliters ($1.5 \times 10^7$)
B. 300 microliters ($6.5 \times 10^7$)
C. 900 microliters (reduced to 300 microliters/dose) ($1.5 \times 10^8$)
D. 4.5 mL (reduced to 300 microliters/dose) ($6.5 \times 10^8$)
E. 9.0 mL ($1.2 \times 10^9$ bacteria) (reduced to 300 microliters/dose)
F. 45.0 mL ($6.5 \times 10^9$ bacteria) reduced to 300 microliters/dose)

The animal observation was performed from day 02 to the tenth day of the assay.

The result is shown in FIG. 12, and it is concluded that the lethal dose is $1.2 \times 10^9$ bacteria and $LD_{50}$ is $6.5 \times 10^8$ bacteria. Renal Quantification of Animals Surviving in the Seventh Day:
A ($1.5 \times 10^7$): no bacterial growth
B ($6.5 \times 10^7$): no bacterial growth
C ($1.5 \times 10^8$): 3100 bacteria
D ($6.5 \times 10^8$): $2.8 \times 10^4$ bacteria 1.3. In Vivo Protection Test—Survival Test—Lethal Dose, Systemic Infection by Intraperitoneal Route in Murine Model The objective of this assay was to evaluate the efficacy of in vivo protection for anti-PBP2a monoclonal antibody against systemic infection with lethal dose, *Enterococcus faecium* (VRE) strain.

1. Antibody (purified from supernatant of the cell culture in medium with serum)
Dialysed and lyophilized purified sample (HPLC SelecSure MAB), resuspended and filtered before use.
Quantification (Lowry's method): 1.0 mg/mL
2. Murine model: female, 8-week Balb/C animals, weigh from 23 to 25 grams
3. Protocol:
group A (6 animals): 650 mg of antibody (350 mg+300 mg)
group B (6 animals): control (saline administration)

4. Preparation of bacterial inoculum:
VRE strain:
pre-inoculum, day 01, 10 mL of BHI broth and vancomycin at 10 mg/mL ON, 37° C., 160 rpm
inoculum, day 03: 300 mL of pre-inoculum in 30 mL of BHI and vancomycin, $DO_{600}$ of 1.31, centrifuged for 10 min, 4,000 rpm, resuspended in sterile PBS 0.5×, adjustment at OD=1.10, dilutions and plates for quantification ($2.0 \times 10^8$ bacteria/mL); inoculum: 12 mL; centrifugate resuspended in 300 mL, IP route (~$2.2 \times 10^9$ bacteria)
Time Schedule:
Day 01: IP inoculation of antibody (350 mg)
Day 02: IP inoculation of antibody (300 mg), systemic infection in the afternoon (IP, 250 mL of bacterial solution—$2.2 \times 10^9$ bacteria)
Day 02 to Day 13: animal observation.

The results are shown in FIG. 13. Only 2 treated animals died (66.6% of protection). All control animals died in the second day.

1.4. In Vivo Protection Test—Systemic Infection by Intraperitoneal Route in Murine Model with Vancomycin-Resistant *Enterococcus faecium* (Results Shown in FIG. 14)

The objective was to evaluate the in vivo protection efficacy of anti-PBP2a and PBP5 monoclonal antibody from enterococci against systemic infection, *E. faecium* (VRE) strain.
Test:
1. Antibody (purified from supernatant of the cell culture in medium with serum)
   Dialysed, lyophilized, and resuspended purified sample (AffiPrep ProteinA Biorad/HPLC SelecSure MAB).
   Quantification (Lowry's method): 1.5 mg/mL
2. Murine model: female, 8-week Balb/C animals, weigh from 19 to 23 grams
3. Protocol:
group A (4 animals): 500 micrograms of antibody (in 2 months, d01, d02)
group B (4 animals): non-protected control
4. Preparation of bacterial inoculum:
Iberian MRSA strain:
pre-inoculum, 10 mL of Lb broth ON, 37° C., 120 rpm
inoculum: 200 microliters of pre-inoculum in 20 mL of Lb, $DO_{600}$ of 0.80, centrifuged for 10 min, 4,000 rpm, resuspended in sterile PBS 0.5×, adjustment at OD=0.51, dilutions and plates for quantification ($2.4 \times 10^8$ bacteria/mL); inoculum: 500 microliters, IP route ($2.4 \times 10^8$ bacteria)
Time Schedule:
Day 01: inoculation of 250 micrograms of antibody by intraperitoneal route
Day 02: inoculation of 250 micrograms of antibody by intraperitoneal route and systemic infection (intraperitoneal, 500 microliters of bacterial solution)
Day 06: euthanasia, bacterial quantification in kidneys
   Based on the results above, we can highlight that:
   In vitro protection assays—determination of minimum inhibitory concentration:
   A total of 700 micrograms of antibody is able to block the growth of 550,000 bacteria. These values are higher than the MIC obtained for MRSA strains, which were approximately 500 micrograms.
In vivo Protection Assays:
In vivo protection test—systemic infection by intraperitoneal route in murine model with sublethal dose of vancomycin-resistant *Enterococcus faecium*.
   The animals received 500 micrograms of monoclonal antibody, intraperitoneal route (IP), and were subjected to systemic infection, IP route, with $2.4 \times 10^8$ bacteria. Four days after, they were subjected to euthanasia and excision of kidneys for bacterial quantification. Treated animals presented a mean of 87.5 bacteria/animal, while controls (non-treated infected animals) presented a mean of 211,000 bacteria/animal.
Survival Test After Lethal Dose Administration
   The animals received 650 micrograms of monoclonal antibody (IP route) and were subjected to systemic infection (IP route) and daily observed for 10 days. Control (non-treated) animals died until the second day after the infection; two of the treated animals (6) died in the second day; the others remained alive until the end of the trial. Survival rate was 66.6%.
   Therefore, once more we have confirmed that MRSA anti-PBPa monoclonal antibody showed to confer cross protection against enterococci. However, the doses needed for conferring protection were higher than the ones used against MRSA in similar conditions. This is probably due to the lower capacity of the antibody to recognize PBP5 with the same efficacy as PBP2a, which it was developed for.
   Therefore, the current invention described here—anti-PBP2a monoclonal antibodies, able to specifically bind to PBP2a and homologous sequences—has applicability in infections caused by bacteria presenting this protein or similar substances (MRSA, MRSE, and *Enterococcus* spp., and any other pathogen that has a protein homologous to PBP2a).
   It is important to emphasize that once these infections are a worldwide problem and the assays were conducted against the main known epidemic MRSA clones, the product of the current invention has application in any place where there are infections by this pathogen.
   The documents relative to the state of the art of knowledge of the inventors, cited in the current descriptive report, are listed below.
1. KOPP, B J. NIX D E, ARMSTRONG E P. Clinical and economic analysis of methicillin-resistant *Staphylococcus aureus* infections. The Annals of Pharmacotherapy; 38:1377-82. 2004.
2. BOYCE, J M. Are the epidemiology and microbiology of methicillin-resistant *Staphylococcus aureus* changing? JAMA; 279(8):623-4. 1998.
3. HUNT, C; DIONNE M, et. al. Four pediatric deaths from community-acquired methicillin-resistant *Staphylococcus aureus* in Minnesota and North Dakota, 1997-1999. Morbidity and Mortality weekly report-CDC USA. 48(32): 707-10. 1999.
4. O'BRIEN, F G; PEARMAN, J W; GRACEY, M; RILEY, T V. GRUBB, W B. Community strain of methicillin-resistant *Staphylococcus aureus* involved in a hospital outbreak. Journal of Clin Microbiol. 37(9):2858-62. 1999.
5. TENOVER, F C; LANCASTER, M V; HILL, B C; STEDWARD, C D; STOCKER, S A; HANCOCK, G A; et. al. Characterization of staphylococci with reduced susceptibilities to vancomycin and other glycopeptides. Journal of Clin Microbiol. 36(4):1020-27. 1998.
6. LUTZ, L; MATOS, S B; KUPLICH, N; MACHADO A; BARTH A L. Caracteristicas laboratoriais de *Staphylococcus aureus* isolado de paciente que nao respondeu ao tratamento com vancomicina. Primeiro Encontro de Controle de Infeccao Hospitalar do MERCOSUL. 1999.
7. COSGROVE, S E; CARROLL, K C; PERL, T M. *Staphylococcus aureus* with reduced susceptibility to vancomycin. Clin Infect Diseases. 39(4):539-45. 2004.
8. JARVIS, W R; SCHLOSSER J M A, CHINN R Y, TWETTEN S, JACSON M. National prevalence of methicillin resistant *Staphylococcus aureus* in inpatients at US health care facilities, 2006. Am J Infect Control. 35(10):631-7. 2007.

9. YAMAUCHI, M. Japan struck by resistant *Staphylococcus aureus*. British Medical Journal. 306:740. 1993.

10. PANLILIO, A L; CULVER, D H; GAYNES, R P. Methicillin-resistant *Staphylococcus aureus* in US hospitals, 1975-1991. Infection Control and Hospital Epid. 13:582-86. 1992.

11. LOWRY, F: *Staphylococcus aureus* infections. New England Journal of Medicine. 339:520-32. 1998.

12. FARR, B M. Prevention and control of methicillin-resistant *Staphylococcus aureus* infections. Current Opinion Infectious Diseases. 17:317-22. 2004.

13. TIEMERSMA, E W; BRONZWA, E R; SLAM, et. al. Methicillin-resistant *Staphylococcus aureus* in Europe, 1999-2002. Emerging Infectious Diseases. 10:1627-34, 2004.

14. BERETTA, ALRZ; TRABASSO, P.; STUCCHI, R B; MORETTI, M L. Use of molecular epidemiology to monitor the nosocomial dissemination of methicillin-resistant *Staphylococcus aureus* in an University hospital from 1991-2001. Braz. Journal of Medical and Biological Research. 37:1345-51. 2004.

15. PANNUTI, C S; GRINBAUM, R S. An overview of nosocomial infection control in Brazil. Infection Control and Hospital Epidemiology. 16(3):170-74. 1995.

16. RESENDE, E M; COUTO, B R G M; STARLING, C E F; MÓDENA, C M. Prevalence of nosocomial infections in general hospitals in Belo Horizonte. Infection Control and Hospital Epidemiology. 19(11):872-76. 1998.

16a. Grundmann H., Aires de Souza M., Boyce J. and Tiemersma J. Emergence and resurgence of Methicillinn-resistant *Staphylococcus aureus* as a public threat health. Lancet. 2006. 368:874-85.

17. GUIGNARD, B; ENTENZA, J M; MOREILLON P. Beta-lactams against methicillin-resistant *Staphylococcus aureus*. Curr. Opin Pharmacol. 5(5):479-89. 2005.

18. SENNA, J P; ROTH, D M; OLIVEIRA, J S; MACHADO, D C, SANTOS D S. Protective immune response against methicillin resistant *Staphylococcus aureus* in a murine model using a DNA vaccine approach. Vaccine. 21:2661-66. 2003.

19. OHWADA, A; SEKIYA, M; HANAKI, H; ARAI, K K; HIRAMATSU, K, FUKUCHI, Y. DNA vaccination by mecA sequence evokes an antibacterial immune response against methicillin-resistant *Staphylococcus aureus*. Antimicrob Agents and Chemother. 44:767-74. 1999.

20. DOMBROWSKI, J C; WINSTON, LG. Clinical failures of appropriately-treated methicillin-resistant *Staphylococcus aureus* infections. J. Infect. 57(2):110-5. 2008.

20bis. RYFFEL, C; TESCH, W; BICH-MACHIN, I.; REYNOLDS, P E; BARBERIS-MAINO, L; KAYSER, F H; BERGER-BACHI, B. Sequence comparison of mecA genes isolated from methicillin-resistant *S. aureus* and *S. epidermidis*. Gene. 94:137-38. 1990.

21. ROTH, D M; SENNA, J P; MACHADO, D C. Evaluation of the humoral immune response in BALB/c mice immunized with a naked DNA vaccine anti-methicillin-resistant *Staphylococcus aureus*. Genetics Molecular Research. 5(3):503-12. 2006.

22. YOKOYAMA, W. Production of monoclonal antibodies: induction of immune responses, p. 2.5.4-2.5.8. In: J. E. Coligan, A. M. Kruisbeek, D. H. Margulies, E. M. Shevach and W. Strober (ed). Current Protocols in Immunology, vol. 1. Wiley and Sons, Hoboken, N.J. 1995.

23. REED, L J AND MUENCH H. Am. J. Hyg. 27:493-97. 1938.

24. KABAT, E A; WU, T T; BILOFSKY, H; M REIDMULLER, PERRY, H. Sequence of proteins of immunological interest. National Institutes of Health, Bethesda. 1993.

25. CHOTIA, C; LESK, A M; TRAMONTANO, A; LEVITT, M; SMITH-GILL, PADLAN, E A; DAVIES, D; TULIP, W R. Conformations of immunoglobulin hypervariable regions. Nature, 342:877-883. 1989.

26. GOULD I M. The clinical significance of methicillin-resistant *Staphylococcus aureus*. J. Hospital Infections, 61(4):277-82. 2005.

27. ANDREMONT, A; TIBON-CORNILLOT, M. Le triomphe des bactéries, la fin des antibiotiques? Ed Max Milo, 1 ed, 2007.

28. Silverstein, Arthur M. Paul Ehrlich's receptor immunology. San Diego: Academic Press, 2002.

29. LIM, D; STRINADKA N C. Structural basis for the beta lactam resistance of PBP2a from methicillin-resistant *Staphylococus aureus*. Nat Struct Biol. 9(11): 870-6. 2002.

30. PAPAKYIRIAKOU, H; VAZ, D; SIMOR, A; LOUIE M; MCGAVIN M J. Molecular analysis of the accessory gene regulator (agr) locus and balance of virulence factor expression in epidemic methicillin-resistant *Staphylococcus aureus*. J Infect Dis. 181(3):2400-4. 2000.

31. TEIXEIRA, L A; RESENDE, C A; ORMONDE, L R; ROSENBAUM, R; FIGUEIREDO A M, DE LENCASTRE H, TOMASZ A. Geographic spread of epidemic multiresistant *Staphylococcus aureus* clone in Brazil. J Clin Microbiol. 33(9):2400-4.1995.

32. DA SILVA, COIMBRA M V; TEIXEIRA, L A; RAMOS, R L; PREDARI, S C; CASTELLO, L; FAMIGLIETTI A, V A, C; KLAN, L; FIGUEIREDO A M. Spread of the Brazilian epidemic clone of a multiresistant MRSA in two cities in Argentina. J Med icrobiol. 49(2):187-92. 2000.

33. SENNA, J P; PINTO, C A; MATEOS, S; QUINTANA, A; SANTOS DS. Spread of a dominant methicillin-resistant *Staphylococcus aureus* (MRSA) clone between Uruguayan and South Brazil Hospitals. J Hospital Infect. 53(2):15607. 2003.

34. MELTER, O; SANTOS SANCHES, I; SCHINDLER, J; AIRES DE SOUZA, M; KOVAROVA, V; ZEMLICKOVA, H; DE LENCASTRE H. Methicillin-resistant *Staphylococcus aureus* clonal types in the Czech Republic. J Clin Microbiol, 37(9):2798-803. 1999.

35. D A SILVA COIMBRA M V, SILVA-CARVALHO M C; WISPLINGHOFF H; HALL G O; TALLENT S; WALLACE, S; EDMOND, M B; FIGUEIREDO, A M; WEINZEL, R P. Clonal spread of methicillin-resistant *Staphylococcus aureus* in a large geographic area of the United States. J Hosp Infect. 53(2):103-10. 2003.

36. NYGAARD, T K; DELEO, F R; VOYICH, J M. Community-associated methicillin-resistant *Staphylococcus aureus* skin infections: advances toward identifying the key virulence factors. Curr Op Infect Dis. 21(2):147-52. 2008.

37. DIEP, B A; CHAMBERS, H F; GRABER, C J; SZUMOWSKI, J D; MILLER, L G; HAN, L L; CHEN, J H; LIN, F; et. al. Emergence of multidrug-resistant, community-associated, methicillin-resistant *Staphylococcus aureus* clone USA300 in men who have sex with men. Ann Intern Med. 148(4):249-57. 2008.

38. REICHERT, J M; DEWITZ, M C. Anti-infective monoclonal antibodies: perils and promise of development. Nat Rev Drug Discov. 5(3):191-5. 2006.

39. GAO, J; STEWART, G C. Regulatory elements of the *Staphylococcus aureus* protein A (Spa) promoter. J. Bacteriol. 186(12):3738-48. 2004.

40. GOFFIN, C; GHUYSEN J M. Multimodular penicillin-binding proteins: an enigmatic family of orthologs and parologs. Microbiol. Mol Biol Rev. 62(4):107.9-93. 1998.

41. COURVALIN P. Vancomycin resistance in gram-positive cocci. Clin Infect Dis. 1; 42 Suppl 1:S25-34. 2006.

42. BAILIE G R, NEAL D. Vancomycin ototoxicity and nephrotoxicity. Med Toxicol Adverse Drug Exp. 3:376-86. 1988.

43. SALGUERO E; PLAZA D; MARINO A; MORENO C; DELGADO G. Characterising vancomycin's immunotoxic profile using Swiss and CFW mice as an experimental model. Biomed Pharmacother. Sep. 16, 2008.

The invention claimed is:

1. An isolated monoclonal antibody capable of binding to PBP2a protein from methicillin-resistant bacteria, said antibody comprising a variable heavy chain possessing a CDR1 region that includes SEQ ID NO:12, a CDR2 region that includes SEQ ID NO:13, a CDR3 region that includes SEQ ID NO:14 and a variable light chain possessing a CDR1 region that includes SEQ ID NO:6, a CDR2 region that includes SEQ ID NO:7 and a CDR3 region that includes SEQ ID NO:8.

2. The antibody of claim 1, wherein the methicillin-resistant bacteria is a strain of *Staphylococcus aureus* resistant to methicillin (MRSA).

3. An isolated monoclonal antibody capable of binding to PBP5 protein from *Enterococcus* spp., said antibody comprising a variable heavy chain possessing a CDR1 region that includes SEQ ID NO:12, a CDR2 region that includes SEQ ID NO:13, a CDR3 region that includes SEQ ID NO:14 and a variable light chain possessing a CDR1 region that includes SEQ ID NO:6, a CDR2 region that includes SEQ ID NO:7 and a CDR3 region that includes SEQ ID NO:8.

4. A pharmaceutical composition comprising a quantity of the isolated monoclonal antibody according to claim 1 and a pharmaceutical vehicle selected from the group consisting of a carrier and an excipient.

5. An isolated monoclonal antibody capable of binding to PBP2a protein from methicillin-resistant bacteria and/or PBP5 protein from *Enterococcus* spp, said antibody comprising a variable heavy chain possessing a CDR1 region that includes the amino acid sequence encoded by SEQ ID NO:15, a CDR2 region that includes the amino acid sequence encoded by SEQ ID NO:16, a CDR3 region that includes the amino acid sequence encoded by SEQ ID NO:17 and a variable light chain possessing a CDR1 region that includes the amino acid sequence encoded by SEQ ID NO:9, a CDR2 region that includes the amino acid sequence encoded by SEQ ID NO:10, and a CDR3 region that includes the amino acid sequence encoded by SEQ ID NO:11.

* * * * *

SEQUENCE LISTING

```
<160> NUMBER OF SEQ ID NOS: 39

<210> SEQ ID NO 1
<211> LENGTH: 668
<212> TYPE: PRT
<213> ORGANISM: Staphylococcus aureus
<220> FEATURE:
<221> NAME/KEY: MISC_FEATURE
<223> OTHER INFORMATION: sequencia de amino acid de PBP2a

<400> SEQUENCE: 1

Met Lys Lys Ile Lys Ile Val Pro Leu Ile Leu Ile Val Val Val Val
1               5                   10                  15

Gly Phe Gly Ile Tyr Phe Tyr Ala Ser Lys Asp Lys Glu Ile Asn Asn
                20                  25                  30

Thr Ile Asp Ala Ile Glu Asp Lys Asn Phe Lys Gln Val Tyr Lys Asp
            35                  40                  45

Ser Ser Tyr Ile Ser Lys Ser Asp Asn Gly Glu Val Glu Met Thr Glu
    50                  55                  60

Arg Pro Ile Lys Ile Tyr Asn Ser Leu Gly Val Lys Asp Ile Asn Ile
65                  70                  75                  80

Gln Asp Arg Lys Ile Lys Lys Val Ser Lys Asn Lys Lys Arg Val Asp
                85                  90                  95

Ala Gln Tyr Lys Ile Lys Thr Asn Tyr Gly Asn Ile Asp Arg Asn Val
                100                 105                 110

Gln Phe Asn Phe Val Lys Glu Asp Gly Met Trp Lys Leu Asp Trp Asp
            115                 120                 125

His Ser Val Ile Ile Pro Gly Met Gln Lys Asp Gln Ser Ile His Ile
        130                 135                 140

Glu Asn Leu Lys Ser Glu Arg Gly Lys Ile Leu Asp Arg Asn Asn Val
145                 150                 155                 160

Glu Leu Ala Asn Thr Gly Thr Ala Tyr Glu Ile Gly Ile Val Pro Lys
                165                 170                 175

Asn Val Ser Lys Lys Asp Tyr Lys Ala Ile Ala Lys Glu Leu Ser Ile
                180                 185                 190

Ser Glu Asp Tyr Ile Lys Gln Gln Met Asp Gln Asn Trp Val Gln Asp
            195                 200                 205

Asp Thr Phe Val Pro Leu Lys Thr Val Lys Lys Met Asp Glu Tyr Leu
    210                 215                 220

Arg Asp Phe Ala Lys Lys Phe His Leu Thr Thr Asn Glu Thr Glu Ser
225                 230                 235                 240

Arg Asn Tyr Pro Leu Gly Lys Ala Thr Ser His Leu Leu Gly Tyr Val
                245                 250                 255

Gly Pro Ile Asn Ser Glu Glu Leu Lys Gln Lys Glu Tyr Lys Gly Tyr
                260                 265                 270

Lys Asp Asp Ala Val Ile Gly Lys Lys Gly Leu Glu Lys Leu Tyr Asp
            275                 280                 285

Lys Lys Leu Gln His Glu Asp Gly Tyr Arg Val Thr Ile Val Asp Asp
```

```
                    290                 295                 300
Asn Ser Asn Thr Ile Ala His Thr Leu Ile Glu Lys Lys Lys Asp
305                 310                 315                 320

Gly Lys Asp Ile Gln Leu Thr Ile Asp Ala Lys Val Gln Lys Ser Ile
                    325                 330                 335

Tyr Asn Asn Met Lys Asn Asp Tyr Gly Ser Gly Thr Ala Ile His Pro
                340                 345                 350

Gln Thr Gly Glu Leu Leu Ala Leu Val Ser Thr Pro Ser Tyr Asp Val
                355                 360                 365

Tyr Pro Phe Met Tyr Gly Met Ser Asn Glu Glu Tyr Asn Lys Leu Thr
370                 375                 380

Glu Asp Lys Lys Glu Pro Leu Leu Asn Lys Phe Gln Ile Thr Thr Ser
385                 390                 395                 400

Pro Gly Ser Thr Gln Lys Ile Leu Thr Ala Met Ile Gly Leu Asn Asn
                405                 410                 415

Lys Thr Leu Asp Asp Lys Thr Ser Tyr Lys Ile Asp Gly Lys Gly Trp
                420                 425                 430

Gln Lys Asp Lys Ser Trp Gly Gly Tyr Asn Val Thr Arg Tyr Glu Val
                435                 440                 445

Val Asn Gly Asn Ile Asp Leu Lys Gln Ala Ile Glu Ser Ser Asp Asn
                450                 455                 460

Ile Phe Phe Ala Arg Val Ala Leu Glu Leu Gly Ser Lys Lys Phe Glu
465                 470                 475                 480

Lys Gly Met Lys Lys Leu Gly Val Gly Glu Asp Ile Pro Ser Asp Tyr
                485                 490                 495

Pro Phe Tyr Asn Ala Gln Ile Ser Asn Lys Asn Leu Asp Asn Glu Ile
                500                 505                 510

Leu Leu Ala Asp Ser Gly Tyr Gly Gln Gly Glu Ile Leu Ile Asn Pro
                515                 520                 525

Val Gln Ile Leu Ser Ile Tyr Ser Ala Leu Glu Asn Asn Gly Asn Ile
                530                 535                 540

Asn Ala Pro His Leu Leu Lys Asp Thr Lys Asn Lys Val Trp Lys Lys
545                 550                 555                 560

Asn Ile Ile Ser Lys Glu Asn Ile Asn Leu Leu Thr Asp Gly Met Gln
                565                 570                 575

Gln Val Val Asn Lys Thr His Lys Glu Asp Ile Tyr Arg Ser Tyr Ala
                580                 585                 590

Asn Leu Ile Gly Lys Ser Gly Thr Ala Glu Leu Lys Met Lys Gln Gly
                595                 600                 605

Glu Thr Gly Arg Gln Ile Gly Trp Phe Ile Ser Tyr Asp Lys Asp Asn
610                 615                 620

Pro Asn Met Met Met Ala Ile Asn Val Lys Asp Val Gln Asp Lys Gly
625                 630                 635                 640

Met Ala Ser Tyr Asn Ala Lys Ile Ser Gly Lys Val Tyr Asp Glu Leu
                645                 650                 655

Tyr Glu Asn Gly Asn Lys Lys Tyr Asp Ile Asp Glu
                660                 665

<210> SEQ ID NO 2
<211> LENGTH: 2007
<212> TYPE: DNA
<213> ORGANISM: Staphylococcus aureus
<220> FEATURE:
<221> NAME/KEY: misc_feature
<223> OTHER INFORMATION: acido nucleico do gene mecA que codifica para
``` a PBP2a

<400> SEQUENCE: 2

| | | | | | | |
|---|---|---|---|---|---|---|
| ttattcatct | atatcgtatt | ttttattacc | gttctcatat | agctcatcat | acactttacc | 60 |
| tgagattttg | gcattgtagc | tagccattcc | tttatcttgt | acatctttaa | cattaatagc | 120 |
| catcatcatg | tttggattat | ctttatcata | tgatataaac | cacccaattt | gtctgccagt | 180 |
| ttctccttgt | ttcattttga | gttctgcagt | accggatttg | ccaattaagt | ttgcataaga | 240 |
| tctataaata | tcttctttat | gtgttttatt | tacgacttgt | tgcataccat | cagttaatag | 300 |
| attgatattt | tctttggaaa | taatattttt | cttccaaact | ttgttttcg | tgtcttttaa | 360 |
| taagtgaggt | gcgttaatat | tgccattatt | ttctaatgcg | ctatagattg | aaaggatctg | 420 |
| tactgggtta | atcagtattt | caccttgtcc | gtaacctgaa | tcagctaata | atatttcatt | 480 |
| atctaaattt | ttgtttgaaa | tttgagcatt | ataaaatgga | taatcacttg | gtatatcttc | 540 |
| accaacacct | agttttttca | tgcctttttc | aaatttctta | ctgcctaatt | cgagtgctac | 600 |
| tctagcaaag | aaaatgttat | ctgatgattc | tattgcttgt | tttaagtcga | tattaccatt | 660 |
| taccacttca | tatcttgtaa | cgttgtaacc | accccaagat | ttatcttttt | gccaaccttt | 720 |
| accatcgatt | ttataacttg | ttttatcgtc | taatgttttg | ttatttaacc | caatcattgc | 780 |
| tgttaatatt | ttttgagttg | aacctggtga | agttgtaatc | tggaacttgt | tgagcagagg | 840 |
| ttctttttta | tcttcggtta | atttattata | ttcttcgtta | ctcatgccat | acataaatgg | 900 |
| atagacgtca | tatgaaggtg | tgcttacaag | tgctaataat | tcacctgttt | gagggtggat | 960 |
| agcagtacct | gagccataat | cattttcat | gttgttataa | atactcttt | gaactttagc | 1020 |
| atcaatagtt | agttgaatat | ctttgccatc | tttttcttt | ttctctatta | atgtatgtgc | 1080 |
| gattgtattg | ctattatcgt | caacgattgt | gacacgatag | ccatcttcat | gttggagctt | 1140 |
| tttatcgtaa | agttttcga | gtcccttttt | accaataact | gcatcatctt | tatagccttt | 1200 |
| atattctttt | tgttttaatt | cttcagagtt | aatgggacca | acataaccta | atagatgtga | 1260 |
| agtcgctttt | tctagaggat | agttacgact | ttctgtttca | ttagttgtaa | gatgaaattt | 1320 |
| ttttgcgaaa | tcacttaaat | attcatccat | tttttaacg | gttttaagtg | gaacgaaggt | 1380 |
| atcatcttgt | acccaatttt | gatccatttg | ttgtttgata | tagtcttcag | aaatacttag | 1440 |
| ttctttagcg | attgctttat | aatctttttt | agatacattc | tttggaacga | tgcctatctc | 1500 |
| atatgctgtt | cctgtattgg | ccaattccac | attgtttcgg | tctaaaattt | taccacgttc | 1560 |
| tgattttaaa | ttttcaatat | gtatgctttg | gtctttctgc | attcctggaa | taatgacgct | 1620 |
| atgatcccaa | tctaacttcc | acataccatc | ttctttaaca | aaattaaatt | gaacgttgcg | 1680 |
| atcaatgtta | ccgtagtttg | ttttaatttt | atattgagca | tctactcgtt | ttttattttt | 1740 |
| agatactttt | tttattttac | gatcctgaat | gtttatatct | ttaacgccta | aactattata | 1800 |
| tatttttatc | ggacgttcag | tcatttctac | ttcaccatta | tcgcttttag | aaatataact | 1860 |
| gctatcttta | taaacttgtt | tgaaatttt | atcttcaatt | gcatcaatag | tattattaat | 1920 |
| ttctttatct | tttgaagcat | aaaaatatat | accaaacccg | acaactacaa | ctattaaaat | 1980 |
| aagtggaaca | attttatct | ttttcat | | | | 2007 |

<210> SEQ ID NO 3
<211> LENGTH: 76
<212> TYPE: PRT
<213> ORGANISM: Staphylococcus aureus
<220> FEATURE:
<221> NAME/KEY: MISC_FEATURE
<223> OTHER INFORMATION: sequencia de amino acido de fragmento de PBP2a

<400> SEQUENCE: 3

Met Tyr Gly Met Ser Asn Glu Glu Tyr Asn Lys Leu Thr Glu Asp Lys
1               5                   10                  15

Lys Glu Pro Leu Leu Asn Lys Phe Gln Ile Thr Thr Ser Pro Gly Ser
            20                  25                  30

Thr Gln Lys Ile Leu Thr Ala Met Ile Gly Leu Asn Asn Lys Thr Leu
        35                  40                  45

Asp Asp Lys Thr Ser Tyr Lys Ile Asp Gly Lys Gly Trp Gln Lys Asp
    50                  55                  60

Lys Ser Trp Gly Gly Tyr Asn Val Thr Arg Tyr Glu
65                  70                  75

<210> SEQ ID NO 4
<211> LENGTH: 4
<212> TYPE: PRT
<213> ORGANISM: Staphylococcus aureus
<220> FEATURE:
<221> NAME/KEY: MISC_FEATURE
<223> OTHER INFORMATION: sequencia de amino acido do centro ativo da
      PBP2a

<400> SEQUENCE: 4

Ser Thr Gln Lys
1

<210> SEQ ID NO 5
<211> LENGTH: 228
<212> TYPE: DNA
<213> ORGANISM: Staphylococcus aureus

<400> SEQUENCE: 5
atgtatggca tgagcaacga agaatataac aaactgaccg aagataaaaa agaaccgctg      60
ctgaacaaat ttcagattac caccagcccg ggcagcaccc agaaaattct gaccgcgatg     120
attggcctga caacaaaac cctggatgat aaaaccagct ataaaattga tggcaaaggc     180
tggcagaaag ataaaagctg gggcggctat aacgtgaccc gctatgaa                 228

<210> SEQ ID NO 6
<211> LENGTH: 16
<212> TYPE: PRT
<213> ORGANISM: Staphylococcus aureus
<220> FEATURE:
<221> NAME/KEY: MISC_FEATURE
<223> OTHER INFORMATION: sequencia de amino acido da cadeia leve para
      CDR1

<400> SEQUENCE: 6

Arg Ser Ser Gln Ser Ile Gly His Ser Asn Gly Asn Thr Tyr Leu Glu
1               5                   10                  15

<210> SEQ ID NO 7
<211> LENGTH: 7
<212> TYPE: PRT
<213> ORGANISM: Staphylococcus aureus
<220> FEATURE:
<221> NAME/KEY: MISC_FEATURE
<223> OTHER INFORMATION: sequencia de amino acido da cadeia leve para
      CDR2

<400> SEQUENCE: 7

Lys Val Ser Asn Arg Phe Ser
1               5

-continued

<210> SEQ ID NO 8
<211> LENGTH: 9
<212> TYPE: PRT
<213> ORGANISM: Staphylococcus aureus
<220> FEATURE:
<221> NAME/KEY: MISC_FEATURE
<223> OTHER INFORMATION: sequencia de amino acido da cadeia leve para
      CDR3

<400> SEQUENCE: 8

Phe Gln Gly Ser Tyr Val Pro Leu Thr
1               5

<210> SEQ ID NO 9
<211> LENGTH: 48
<212> TYPE: DNA
<213> ORGANISM: Staphylococcus aureus
<220> FEATURE:
<221> NAME/KEY: misc_feature
<223> OTHER INFORMATION: sequencia de DNA da cadeia leve para CDR1

<400> SEQUENCE: 9
cgcagcagcc agagcattgg ccatagcaac ggcaacacct atctggaa                 48

<210> SEQ ID NO 10
<211> LENGTH: 21
<212> TYPE: DNA
<213> ORGANISM: Staphylococcus aureus
<220> FEATURE:
<221> NAME/KEY: misc_feature
<223> OTHER INFORMATION: sequencia de DNA da cadeia leve para CDR2

<400> SEQUENCE: 10
aaagtgagca accgctttag c                                              21

<210> SEQ ID NO 11
<211> LENGTH: 27
<212> TYPE: DNA
<213> ORGANISM: Staphylococcus aureus
<220> FEATURE:
<221> NAME/KEY: misc_feature
<223> OTHER INFORMATION: sequencia de DNA da cadeia leve para CDR3

<400> SEQUENCE: 11
tttcagggca gctatgtgcc gctgacc                                        27

<210> SEQ ID NO 12
<211> LENGTH: 12
<212> TYPE: PRT
<213> ORGANISM: Staphylococcus aureus
<220> FEATURE:
<221> NAME/KEY: MISC_FEATURE
<223> OTHER INFORMATION: sequencia de amino acido da cadeia pesada para
      CDR1

<400> SEQUENCE: 12

Gly Phe Ser Ile Thr Ser Ser Ser Ser Cys Trp His
1               5                   10

<210> SEQ ID NO 13
<211> LENGTH: 16
<212> TYPE: PRT
<213> ORGANISM: Staphylococcus aureus
<220> FEATURE:
<221> NAME/KEY: MISC_FEATURE
<223> OTHER INFORMATION: sequencia de amino acido da cadeia pesada para
      CDR2

<400> SEQUENCE: 13

Arg Ile Cys Tyr Glu Gly Ser Ile Ser Tyr Ser Pro Ser Leu Lys Ser
1               5                   10                  15

<210> SEQ ID NO 14
<211> LENGTH: 9
<212> TYPE: PRT
<213> ORGANISM: Staphylococcus aureus
<220> FEATURE:
<221> NAME/KEY: MISC_FEATURE
<223> OTHER INFORMATION: sequencia de amino acido da cadeia pesada para
      CDR3

<400> SEQUENCE: 14

Glu Asn His Asp Trp Phe Phe Asp Val
1               5

<210> SEQ ID NO 15
<211> LENGTH: 36
<212> TYPE: DNA
<213> ORGANISM: Staphylococcus aureus
<220> FEATURE:
<221> NAME/KEY: misc_feature
<223> OTHER INFORMATION: sequencia de DNA da cadeia pesada para CDR1

<400> SEQUENCE: 15
ggctttagca ttaccagcag cagcagctgc tggcat                        36

<210> SEQ ID NO 16
<211> LENGTH: 48
<212> TYPE: DNA
<213> ORGANISM: Staphylococcus aureus
<220> FEATURE:
<221> NAME/KEY: misc_feature
<223> OTHER INFORMATION: sequencia de DNA da cadeia pesada para CDR2

<400> SEQUENCE: 16
cgcatttgct atgaaggcag cattagctat agcccgagcc tgaaaagc            48

<210> SEQ ID NO 17
<211> LENGTH: 27
<212> TYPE: DNA
<213> ORGANISM: Staphylococcus aureus
<220> FEATURE:
<221> NAME/KEY: misc_feature
<223> OTHER INFORMATION: sequencia de DNA da cadeia pesada para CDR3

<400> SEQUENCE: 17
gaaaaccatg attggttttt tgatgtg                                  27

<210> SEQ ID NO 18
<211> LENGTH: 33
<212> TYPE: DNA
<213> ORGANISM: Staphylococcus aureus

<400> SEQUENCE: 18
atggaagctt gctgggtcta caagctgtgg att                           33

<210> SEQ ID NO 19
<211> LENGTH: 30
<212> TYPE: DNA
<213> ORGANISM: Staphylococcus aureus

<400> SEQUENCE: 19
atggaaatgg cagcctggtc ttattcctct                               30

```
<210> SEQ ID NO 20
<211> LENGTH: 20
<212> TYPE: DNA
<213> ORGANISM: Staphylococcus aureus

<400> SEQUENCE: 20
gatgtgaagc ttcaggagtc                                              20

<210> SEQ ID NO 21
<211> LENGTH: 20
<212> TYPE: DNA
<213> ORGANISM: Staphylococcus aureus

<400> SEQUENCE: 21
caggtgcagc tgaaggagtc                                              20

<210> SEQ ID NO 22
<211> LENGTH: 20
<212> TYPE: DNA
<213> ORGANISM: Staphylococcus aureus

<400> SEQUENCE: 22
caggtgcagc tgaagcagtc                                              20

<210> SEQ ID NO 23
<211> LENGTH: 20
<212> TYPE: DNA
<213> ORGANISM: Staphylococcus aureus

<400> SEQUENCE: 23
caggttactc tgaaagagtc                                              20

<210> SEQ ID NO 24
<211> LENGTH: 21
<212> TYPE: DNA
<213> ORGANISM: Staphylococcus aureus

<400> SEQUENCE: 24
gaggtccagc tgcaacaatc t                                            21

<210> SEQ ID NO 25
<211> LENGTH: 20
<212> TYPE: DNA
<213> ORGANISM: Staphylococcus aureus

<400> SEQUENCE: 25
gaggtccagc tgcagcagtc                                              20

<210> SEQ ID NO 26
<211> LENGTH: 21
<212> TYPE: DNA
<213> ORGANISM: Staphylococcus aureus

<400> SEQUENCE: 26
caggtccaac tgcagcagcc t                                            21

<210> SEQ ID NO 27
<211> LENGTH: 20
<212> TYPE: DNA
<213> ORGANISM: Staphylococcus aureus

<400> SEQUENCE: 27
```

```
gaggtgaagc tggtggagtc                                               20

<210> SEQ ID NO 28
<211> LENGTH: 20
<212> TYPE: DNA
<213> ORGANISM: Staphylococcus aureus

<400> SEQUENCE: 28
gatgtgaact tggaagtgtc                                               20

<210> SEQ ID NO 29
<211> LENGTH: 29
<212> TYPE: DNA
<213> ORGANISM: Staphylococcus aureus

<400> SEQUENCE: 29
tggacaggga tccagagttc caggtcact                                     29

<210> SEQ ID NO 30
<211> LENGTH: 21
<212> TYPE: DNA
<213> ORGANISM: Staphylococcus aureus

<400> SEQUENCE: 30
gacattgtga tgacccagtc t                                             21

<210> SEQ ID NO 31
<211> LENGTH: 21
<212> TYPE: DNA
<213> ORGANISM: Staphylococcus aureus

<400> SEQUENCE: 31
gatgttttga tgacccaaac t                                             21

<210> SEQ ID NO 32
<211> LENGTH: 18
<212> TYPE: DNA
<213> ORGANISM: Staphylococcus aureus

<400> SEQUENCE: 32
gatattgtga taacccag                                                 18

<210> SEQ ID NO 33
<211> LENGTH: 21
<212> TYPE: DNA
<213> ORGANISM: Staphylococcus aureus

<400> SEQUENCE: 33
gacattgtgc tgacccaatc t                                             21

<210> SEQ ID NO 34
<211> LENGTH: 21
<212> TYPE: DNA
<213> ORGANISM: Staphylococcus aureus

<400> SEQUENCE: 34
gatattgtgc taactcagtc t                                             21

<210> SEQ ID NO 35
<211> LENGTH: 21
<212> TYPE: DNA
<213> ORGANISM: Staphylococcus aureus

<400> SEQUENCE: 35
```

```
gatatccaga tgacacagac t                                               21

<210> SEQ ID NO 36
<211> LENGTH: 21
<212> TYPE: DNA
<213> ORGANISM: Staphylococcus aureus

<400> SEQUENCE: 36
gacatccagc tgactcagtc t                                               21

<210> SEQ ID NO 37
<211> LENGTH: 21
<212> TYPE: DNA
<213> ORGANISM: Staphylococcus aureus

<400> SEQUENCE: 37
caaattgttc tcacccagtc t                                               21

<210> SEQ ID NO 38
<211> LENGTH: 21
<212> TYPE: DNA
<213> ORGANISM: Staphylococcus aureus

<400> SEQUENCE: 38
caggctgttg tgactcagga a                                               21

<210> SEQ ID NO 39
<211> LENGTH: 18
<212> TYPE: DNA
<213> ORGANISM: Staphylococcus aureus

<400> SEQUENCE: 39
tacagttggt gcagcatc                                                   18
```